US010194837B2

(12) United States Patent
Kanchan et al.

(10) Patent No.: US 10,194,837 B2
(45) Date of Patent: Feb. 5, 2019

(54) DEVICES FOR MEASURING HUMAN GAIT AND RELATED METHODS OF USE

(71) Applicant: Vayu Technology Corp., Los Angeles, CA (US)

(72) Inventors: Karan Harish Kanchan, Los Angeles, CA (US); Prathamesh Mantri, Los Angeles, CA (US)

(73) Assignee: Vayu Technology Corp., Los Angeles, CA (US)

( * ) Notice: Subject to any disclaimer, the term of this patent is extended or adjusted under 35 U.S.C. 154(b) by 0 days.

(21) Appl. No.: 15/151,557

(22) Filed: May 11, 2016

(65) Prior Publication Data

US 2016/0338621 A1 Nov. 24, 2016

Related U.S. Application Data

(60) Provisional application No. 62/247,880, filed on Oct. 29, 2015, provisional application No. 62/179,786, filed on May 18, 2015.

(51) Int. Cl.
*A61B 5/11* (2006.01)
*A61B 5/103* (2006.01)
(Continued)

(52) U.S. Cl.
CPC .............. *A61B 5/112* (2013.01); *A61B 5/002* (2013.01); *A61B 5/0022* (2013.01);
(Continued)

(58) Field of Classification Search
CPC .... A61B 5/11; A61B 2562/164; A61B 5/0022
See application file for complete search history.

(56) References Cited

U.S. PATENT DOCUMENTS 8,109,890 B2 2/2012 Kamiar et al.
8,172,722 B2 5/2012 Molyneux et al.
(Continued)

FOREIGN PATENT DOCUMENTS

CN 202932930 U 5/2013
JP 2001258870 A1 * 9/2001
(Continued)

OTHER PUBLICATIONS

Machine Translation of JP2001-258870.*
(Continued)

*Primary Examiner* — Christopher D Koharski
*Assistant Examiner* — Amanda Steinberg
(74) *Attorney, Agent, or Firm* — Loza & Loza, LLP; Heidi L. Eisenhut

(57) ABSTRACT

A portable, wearable multi-component measurement and analysis device can be utilized for collecting and analyzing bio-mechanical and human gait analysis data while performing any physical activity. This device may be constructed with one or more sensors that are placed on the various localities of human body to collect bio-mechanical data. This data may be transmitted over a network to a server, where it is analyzed, and feedback may be provided in real time on the bio-mechanical and gait parameters experienced by the user's body while performing any particular activity. The device further may allow specialists and experts located anywhere in the world to analyze this real time data and give feedback.

20 Claims, 17 Drawing Sheets

(51) Int. Cl.
*A61B 5/00* (2006.01)
*G06F 19/00* (2018.01)
*G16H 40/67* (2018.01)

(52) U.S. Cl.
CPC .......... *A61B 5/0024* (2013.01); *A61B 5/1036* (2013.01); *A61B 5/11* (2013.01); *A61B 5/4528* (2013.01); *A61B 5/486* (2013.01); *A61B 5/6802* (2013.01); *A61B 5/6806* (2013.01); *A61B 5/6807* (2013.01); *G06F 19/00* (2013.01); *G16H 40/67* (2018.01); *A61B 5/6812* (2013.01); *A61B 5/6823* (2013.01); *A61B 5/6824* (2013.01); *A61B 5/6825* (2013.01); *A61B 5/6828* (2013.01); *A61B 5/6829* (2013.01); *A61B 5/742* (2013.01); *A61B 2503/10* (2013.01); *A61B 2562/0219* (2013.01); *A61B 2562/0223* (2013.01); *A61B 2562/0247* (2013.01); *A61B 2562/164* (2013.01)

(56) References Cited

U.S. PATENT DOCUMENTS

| | | | | |
|---|---|---|---|---|
| 8,616,989 | B2* | 12/2013 | Bentley | A61B 5/1122 473/207 |
| 8,707,463 | B2 | 4/2014 | Orloff | |
| 8,740,752 | B2* | 6/2014 | Ellis | A61B 5/1038 482/1 |
| 8,840,527 | B2* | 9/2014 | Zhang | A61B 5/4595 482/8 |
| 8,868,369 | B2 | 10/2014 | Esser et al. | |
| 9,149,222 | B1* | 10/2015 | Zets | A61B 5/16 |
| 9,311,789 | B1* | 4/2016 | Gwin | G08C 19/00 |
| 2005/0209535 | A1* | 9/2005 | Dariush | A61B 5/4528 600/595 |
| 2010/0121228 | A1 | 5/2010 | Stirling et al. | |
| 2010/0185398 | A1 | 7/2010 | Berns et al. | |
| 2011/0218463 | A1 | 9/2011 | Hodgins et al. | |
| 2011/0230986 | A1* | 9/2011 | Lafortune | A43B 3/0005 700/93 |
| 2012/0172126 | A1 | 7/2012 | Padovani et al. | |
| 2013/0217998 | A1* | 8/2013 | Mahfouz | A61B 8/4263 600/409 |
| 2013/0281815 | A1 | 10/2013 | Varadan | |
| 2014/0156218 | A1* | 6/2014 | Kim | A61B 5/1114 702/150 |
| 2014/0195023 | A1* | 7/2014 | Statham | A63B 69/0028 700/91 |
| 2014/0343861 | A1 | 11/2014 | Edman et al. | |
| 2014/0375465 | A1* | 12/2014 | Fenuccio | G08B 5/36 340/691.1 |
| 2015/0018722 | A1 | 1/2015 | Yanev | |
| 2015/0066173 | A1* | 3/2015 | Ellis | A61B 5/1038 700/91 |
| 2015/0075303 | A1* | 3/2015 | Connor | A61B 5/1126 73/865.4 |
| 2015/0201867 | A1* | 7/2015 | Peindl | A61B 5/1118 600/595 |
| 2016/0220808 | A1* | 8/2016 | Hyde | A61N 1/0452 |
| 2016/0256082 | A1* | 9/2016 | Ely | A61B 5/0024 |
| 2016/0262685 | A1* | 9/2016 | Wagner | A61B 5/1101 |

FOREIGN PATENT DOCUMENTS

| | | | |
|---|---|---|---|
| WO | WO-2014/145361 | A1 | 9/2014 |
| WO | 2015017712 | A1 | 2/2015 |

OTHER PUBLICATIONS

Sep. 19, 2016 (PCT) Invitation to Pay Additional Fees and Partial International Search Report issued in International App. No. PCT/US2016/031708, 9 pages.
2010—Chen, S. et al., "Mister Gloves—A Wireless USB Gesture Input System," XP002760146, retrieved Jul. 21, 2016, from https://courses.cit.cornell.edu/ee476/FinalProjects/s2010/ssc88_egl27/.
"Athos" retrieved from the Internet URL: http://www.liveathos.com on Aug. 29, 2016.
"Catapult" retrieved from the Internet URL: http://www.catapultsports.com on Aug. 29, 2016.
"Enflux" retrieved from the Internet URL: http://www.enfluxvr.com on Aug. 29, 2016.
"Fitbit" retrieved from the Internet URL: http://fitbit.com on Aug. 29, 2016.
"Heddoko" retrieved from the Internet URL: http://heddoko.com on Aug. 29, 2016.
"I Measure U" retrieved from the Internet URL: http://imeasureu.com on Aug. 29, 2016.
"Nike fuel band" retrieved from the Internet URL: http://www.nike.com/us/en_us/c/nikeplus/nikefuel on Aug. 29, 2016.
"Noraxon—myoMotion" retrieved from the Internet URL: http://www.noraxon.com/products/3d-motion-capture on Aug. 29, 2016.
"Xsens" retrieved from the Internet URL: http://www.xsens.com on Aug. 29, 2016.

* cited by examiner

DEVICES FOR MEASURING HUMAN GAIT AND RELATED METHODS OF USE

CROSS REFERENCE TO RELATED APPLICATION(S)

This application claims priority to U.S. Provisional Patent Application No. 62/179,786, filed May 18, 2015, and U.S. Provisional Patent Application No. 62/247,880, filed Oct. 29, 2015. The entirety of each of the above-referenced applications is incorporated by reference herein.

TECHNICAL FIELD

Various examples of the present disclosure relate to the field of bio-mechanics and/or human gait analysis. More particularly, the disclosure relates to a device wearable by a user while performing any particular activity.

BACKGROUND

Currently, gait analysis is conducted in a lab setting with high speed cameras and force plates. Luminescent markers may be used, which may be bulky, complex, and expensive. The existing configuration has mobility challenges and provides limited, time based data for any activity. The current mechanism that tracks human activity, mobility, and posture over a defined period (e.g., 15 to 20 minutes in a lab) is not sufficient to provide a thorough and robust source of data for analysis. The mechanical devices used to gather the necessary data to make analytical assessments may contribute to the deficiencies of the current methods.

Accordingly, there is a need for less expensive, more convenient, and more robust measurement and/or analysis devices and systems that provide clearer and more accurate data.

SUMMARY

Embodiments of the present disclosure relate to, among other things, devices for measuring human gait and related methods of use. Each of the embodiments disclosed herein may include one or more of the features described in connection with any of the other disclosed embodiments.

A system for collecting data related to user movements may include a plurality of wearable garments, wherein each garment includes at least one sensor configured to collect data related to movement of a corresponding portion of the user; one or more data storage devices storing instructions for processing the data; and one or more processors configured to execute the instructions to perform a method, including: for each at least one sensor, analyzing the data to determine an orientation of the corresponding portion of the user within a user-specific coordinate system; and providing feedback to the user.

The system may additionally or alternatively include one or more of the following features: the user-specific coordinate system may be determined based, at least in part, on a height of the user and a waist size of the user; at least one of the plurality of wearable garments may include a sleeve configured to be positioned on at least one of an arm or a leg of the user, wherein a first sensor of the at least one sensor configured to collect data may be configured to be positioned on a first side of a joint, and a second sensor of the at least one sensor may be configured to be positioned on a second side of a joint; at least one of the plurality of wearable garments may include a sock configured to be positioned on a foot of the user, wherein the at least one sensor configured to collect data may be configured to be positioned adjacent a dorsal surface of the foot, and the sock may further include a plurality of pressure sensors configured to be positioned adjacent a plantar surface of the foot; at least one of the plurality of wearable garments may include a glove configured to be positioned on a hand of the user, wherein the at least one sensor configured to collect data may be configured to be positioned adjacent a dorsal surface of the hand, and the glove may further include a plurality of pressure sensors configured to be positioned adjacent a palmar surface of the hand; at least one of the plurality of wearable garments may include a chest piece; each garment may include a wireless transmitter configured to transmit the data collected by the at least one sensor; the at least one sensor may include at least one of an accelerometer, a gyroscope, and a magnetometer; and providing feedback to the user may include displaying information related to one or more of: ground reaction force, body portion orientation, total body orientation, joint force, joint torque, or segment fatigue.

In another example, a system for collecting data related to user movements may include a plurality of wearable garments, wherein each garment includes at least one sensor configured to collect data related to movement of a corresponding portion of the user, wherein the plurality of wearable garments includes: a sleeve configured to be positioned on at least one of an arm or a leg of the user, wherein a first sensor of the at least one sensor configured to collect data is configured to be positioned on a first side of a joint, and a second sensor of the at least one sensor is configured to be positioned on a second side of a joint; a sock configured to be positioned on a foot of the user, wherein the at least one sensor configured to collect data is configured to be positioned adjacent a dorsal surface of the foot, and the sock further includes a plurality of pressure sensors configured to be positioned adjacent a plantar surface of the foot; a glove configured to be positioned on a hand of the user, wherein the at least one sensor configured to collect data is configured to be positioned adjacent a dorsal surface of the hand, and the glove further includes a plurality of pressure sensors configured to be positioned adjacent a palmar surface of the hand; and a chest piece.

The system may additionally or alternatively include one or more of the following features: the sleeve may be a first sleeve configured to be positioned on a left arm of the user, and the system may further include a second sleeve configured to be positioned on a right arm of the user, a third sleeve configured to be positioned on a left leg of the user, and a fourth sleeve configured to be positioned on a right leg of the user; the sock may be a first sock and the foot may be a left foot, and the system may further include a second sock configured to be positioned on a right foot of the user; and the glove may be a first glove and the hand may be a left hand, and the system may further include a second glove configured to be positioned on a right hand of the user; the at least one sensor configured to collect data may include at least one of an accelerometer, a gyroscope, and a magnetometer; a first pressure sensor of the plurality of pressure sensors of the sock may be configured to be positioned adjacent a heel of the foot, and a second pressure sensor and a third pressure sensor of the plurality of pressure sensors of the sock may be configured to be positioned adjacent a ball of the foot; the chest piece may include a hub, and the hub may be configured to receive the data from the sleeve, the sock, and the glove; each garment may include a wireless transmitter configured to transmit the data collected by the at least one sensor; and the at least one sensor of each garment may be operatively connected to: a memory, a micro-controller with a wireless communication module, and a battery.

In yet another example, a method for collecting data related to user movements may include positioning each of a plurality of wearable garments in contact with a corresponding portion of the user, wherein each garment includes at least one sensor configured to collect data related to movement of the corresponding portion of the user; collecting the data related to each corresponding portion of the user while the user performs an activity; transmitting the data via a wireless communication network to one or more servers; using the one or more servers, developing a user-specific coordinate system and determining an orientation of each corresponding portion of the user within the user-specific coordinate system; and providing feedback to the user.

The method may additionally or alternatively include one or more of the following features or steps: providing feedback to the user may include displaying information related to one or more of: ground reaction force, body portion orientation, total body orientation, joint force, joint torque, or segment fatigue; the plurality of wearable garments may include at least one arm sleeve, at least one leg sleeve, at least one sock, at least one glove, and a chest piece; and the method may further include collecting pressure data from at least one of the plurality of garments.

It may be understood that both the foregoing general description and the following detailed description are exemplary and explanatory only and are not restrictive of the invention, as claimed.

BRIEF DESCRIPTION OF THE FIGURES

The accompanying drawings, which are incorporated in and constitute a part of this specification, illustrate various examples and together with the description, serve to explain the principles of the disclosed examples.

DETAILED DESCRIPTION

Figure 1:
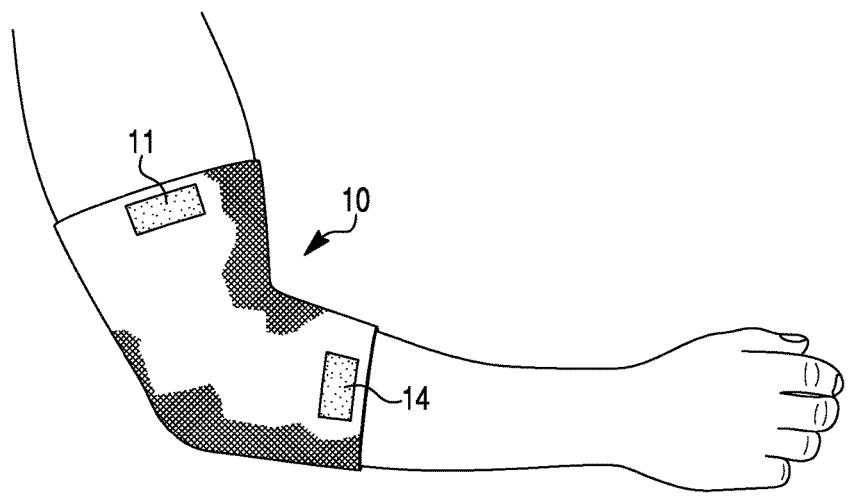
FIG. 1 is an arm sleeve according to an example of the present disclosure.

Reference will now be made in detail to examples of the present disclosure, which are illustrated in the accompanying drawings. Wherever possible, the same reference numbers will be used throughout the drawings to refer to the same or like parts.

As used herein, the terms "comprises," "comprising," or any other variation thereof, are intended to cover a non-exclusive inclusion, such that a process, method, article, or apparatus that comprises a list of elements does not include only those elements, but may include other elements not expressly listed or inherent to such process, method, article, or apparatus. The term "exemplary" is used in the sense of "example," rather than "ideal."

This disclosure provides sophisticated engineering to positively contribute to one or more of the fields of bio-mechanics, gait analysis, and any other domain that requires measurement and/or analysis of human body motion. Devices and methods of the present disclosure may allow users to avoid travel time to an analysis lab, expand consultation with doctors beyond geographic constraints, provide the freedom to measure and/or analyze a variety of physical activities over a longer period of time, and provide the freedom to conduct measurements and/or analysis at convenient times and locations for the user, such as in the natural environment of the analyzed activity and/or daily routine. Each of the embodiments described herein may include one or more of the features described in connection with any of the embodiments described herein.

Wearable Devices

Examples of the present disclosure include systems and methods that use single and/or multi-component wearable devices (e.g., garments) that work together, interdependently, or independently to collect, analyze, and/or give feedback on a user's bio-mechanical activity while the user is performing any particular exercise. A garment, as used herein, may be any object configured to be worn by a user (e.g., clothing, wraps, straps, hats, gloves, etc.). The garment may be self-securing (e.g., an arm sleeve may include elastic or may be sized to fit snugly around the user's arm), or the garment may be secured to the user by an adhesive or by any other method. In one example, the system may include one or more of the following garments/wearable devices: arm sleeves 10 (FIG. 1), gloves 20 (FIGS. 2A and 2B), leg sleeves 30 (FIG. 3), socks 40 (FIGS. 4 and 5), and a chest piece 50 (FIG. 6). The devices may form the kit 600 shown in FIG. 6.

Figure 7:
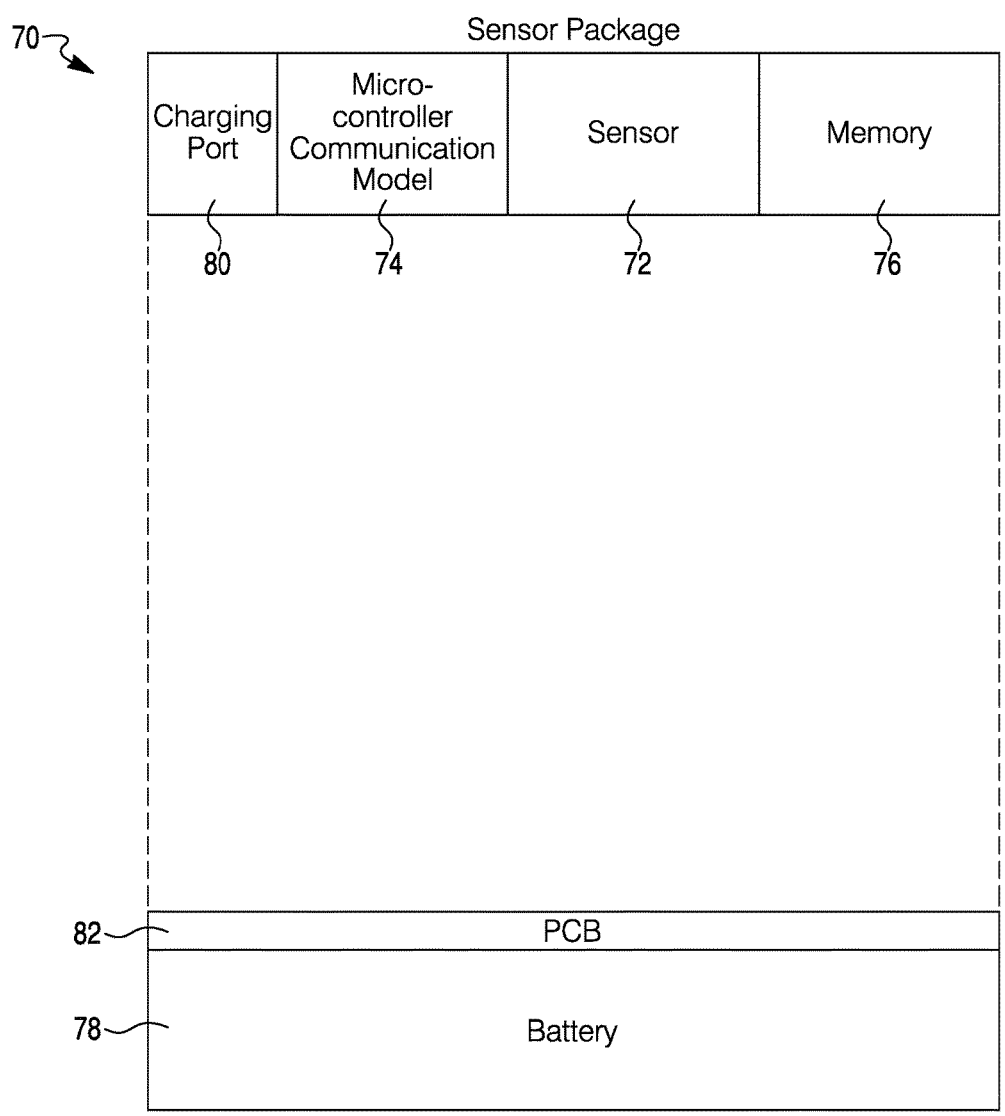
FIG. 7 is a schematic of a sensor package according to an example of the present disclosure.

Each wearable device described herein may include one or more sensors. The sensors may be included within a sensor package having one or more sensors along with other components, or the sensors may be individual pressure sensors or other types of sensors. An exemplary sensor package 70 is shown in FIG. 7. The sensor packages described in connection with the wearable devices herein may the same as or may include different components than sensor package 70. The sensor package 70 may include one or more sensors 72. The sensor 72 may be a force and/or IMU (inertial measurement unit) sensor. The sensor package 70 may further include a processor 74 (e.g., an ARM-based microcontroller), a wireless or wired transmitter (e.g., a low energy module which may support Bluetooth Low Energy (BLE) or Wi-Fi) (included within processor 74), a memory chip 76, a battery 78, a charging port 80, and a primary circuit board 82. Sensors may be mounted on primary circuit board 82, which may be flexible and may conform to the curvature of the body. In some embodiments, one or more of the memory chip, wireless transmitter, and charging port may be omitted. For example, charging port may be replaced with a replaceable battery, or a wireless charging module. The sensor package may be encased in a waterproof casing/covering. In one example, one or more sensors 72 within sensor package 70 may include one or more of an accelerometer, a gyroscope, and a magnetometer. These components may facilitate calculation of a body's center of mass.

In some examples, the wearable devices may include multi-color LEDs, whose colors may change according to the status of the device. For example, a first color may be displayed when the device is collecting data, a second color may be displayed when the device is connected to a power source, a third color may be displayed while the device is disconnected, a fourth color may be displayed when the device has a low battery, and a fifth color may be displayed when the device is transmitting data. The wearable devices may be portable and reusable.

The sensors may be located at key points of the human body and collect valuable bio-mechanical data. At least two different types of sensors may be used in various locations to collect data. Orientation (IMU) sensors may include an accelerometer, a gyroscope and a magnetometer. Resistive or capacitive force sensors also may be used. The sensors may or may not be activated with body heat in some examples. The various sensors may be configured to collect data in at least three dimensions (e.g., along at least three axes).

The user discussed herein refers to any person. For example, users may be professional athletes, budding athletes, patients (e.g., pre and post surgery), orthopedics, or any person desiring to measure and/or analyze his or her own gait or movement characteristics. Any particular exercise may include any activity, such as, for example, walking, jogging, running, cycling, playing a sport (like tennis, basketball, football, baseball, or the like), physical workout and/or training, and water activities such as, e.g., swimming, etc. Devices of the present disclosure may be configured to measure and analyze biomechanical parameters on land, in water, or in the air. In some examples, a triathlete may be analyzed at the different portions of a triathlon with the same set of devices. Because the devices can be used on both water and land, a triathlete can be measured and analyzed during the swim, bike, and run portions of a triathlon.

The particular sensor arrangements described herein may be made to strategically collect all required inputs as well as to minimize any discomfort experienced by the user in terms of the size of the sensors and their respective positioning. The sensor arrangements may allow for the user to experience natural movement, which may ensure the validity and accuracy of the measurement and analysis.

In some examples, a heart rate monitor may be used to collect data to help attain a more complete view of an athlete's or patient's respiratory performance along with his or her biomechanical system. The heart rate data may be combined with biomechanical data, for example, to help determine fatigue (e.g., an increase in heart rate over time may further indicate fatigue). Other physiologic sensors also may be used to obtain data that can be analyzed and/or presented with the biomechanical data. These include, for example, oxygen saturation, blood glucose, temperature, ECG, etc.

Any of the wearable garments described herein may be waterproof and made to/intended to fit the relevant portions of the user's body (e.g., right arm and forearm, left arm and forearm, right hand, left hand, right thigh and shank, left thigh and shank, right foot, and left foot, and chest). The garments may be compression garments and may include fabric that absorbs liquid. For example, the garments and/or fabric may be sweat-resistant, water-compatible, breathable, and comfortable. However, any sensors (e.g., sensors within sensor packages, pressure sensors) and all other electrical components may be waterproof to at least 10 meters according to conventional waterproofing mechanisms. The garments may have one or more sensor packages that may be strategically placed to measure data related to a body portion's movement and/or contact with other objects. The sensors may be placed on an inner surface of the garment (e.g., contacting the user's skin), may be embedded within layers of the garment, or or may rest on an outer surface of the garment.

The sensors may measure movement data that the various body portions experience (e.g., right arm and forearm, left arm and forearm, right hand, left hand, right thigh and shank, left thigh and shank, right foot, and left foot, and chest). The combination or individual collection of measurements from all portions of the body may be sent/transmitted to a hub using a wireless communication protocol. This data then may be transferred from the hub to cloud/backend servers where an algorithm conducts the biomechanical analysis of the body portions. The data stream may include the acceleration experienced by the body, the angular velocity, and the orientation of the body with respect to the earth's magnetic field. The data stream also may include the force experienced by the feet and hands, which may be collected by or calculated from data collected by the gloves and socks (e.g., by pressure sensors). Filters (e.g., low-pass filters) may be applied to remove noise from the data. All or some of the collected data may be merged to determine the orientation of the body. In some examples, all of the collected data may be used. Depending on the patterns of the data collected, systems of the present disclosure may analyze what movement the body is conducting and determine the orientation of the body in three dimensional space. In some examples, no intermediate determinations may be made. However, a final holistic and comprehensive biomechanical analysis may be performed.

Referring to FIG. 1, an arm sleeve 10 is shown. The arm sleeve 10 may be worn on either the left or right arm. It is contemplated that the user may wear an arm sleeve 10 on each arm or only on one of the right and left arms. Likewise, for the other embodiments described herein, the user may wear the described device on one or multiple body parts, as desired or prescribed.

The arm sleeve 10 may include two sensor packages 11 and 14, although any other suitable number of sensor packages may be utilized. When worn by a user, first sensor package 11 may be positioned on the bicep of a user, and second sensor package 14 may be positioned on the forearm. Sensor packages 11, 14 may be positioned on the lateral surface of the right arm and forearm and left arm and forearm in an anatomical position. However, the sensors may be positioned on any surface of the arm/forearm. For example, each sensor package 11, 14 may alternatively be positioned on the medial surface, anterior surface, or posterior surface of the arm/forearm. In one example, first sensor package 11 is configured to be positioned on a first side of a joint (e.g., the elbow), and second sensor package 14 is configured to be positioned on a second side of the joint.

Figure 2A:
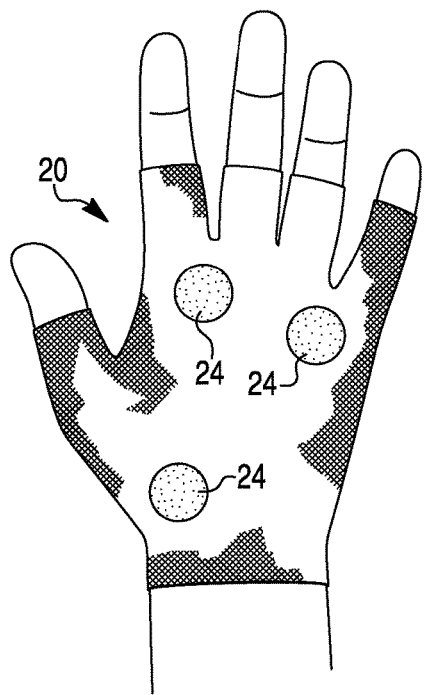
FIG. 2A is a palm view of a glove according to the present disclosure.
Figure 2B:
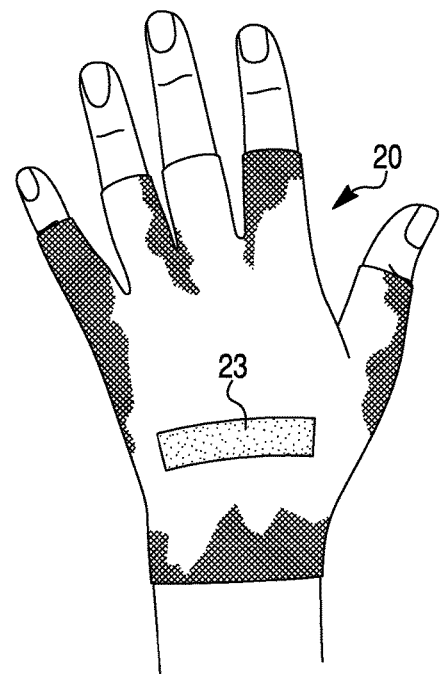
FIG. 2B is a dorsal view of the glove of FIG. 2A.

In FIGS. 2A and 2B, a left-handed glove 20 is shown. The system may further include a similar glove for the right hand. The glove 20 may include one sensor package 23 on the dorsal side of glove 20. The dorsal sensor package 20 may be an orientation or IMU sensor package and may measure movement data that the right and/or left hands experience. More or less sensor packages may be provided, as desired. The glove 20 may include three pressure sensors 24 on the palmar side of the glove 20. A first pressure sensor 24 may be positioned on the palm underneath the index and/or middle finger. A second pressure sensor 24 may be positioned on the palm underneath the ring and/or pinkie finger. A third pressure sensor 24 may be positioned proximally relative to the first pressure sensor 24 on the palm, closer to the wrist and at the base of the thumb. The pressure sensors may be placed strategically at the contact points of the palm (and feet, as described below) instead of in random locations. Those of ordinary skill in the art will understand that other suitable sensor position configurations may be utilized within the principles of the present disclosure. In some examples, complete palm/hand and/or foot mapping may be achieved using a matrix of sensors to help enable orthotics experts to design custom orthotics remotely.

In some examples, the gloves 20 may be able to help sense external factors, such as, e.g., that weights are being carried by the user in the gym or weight room, so that the analysis may account for those parameters and include them in the analysis. An athlete's gait may be affected by having to carry heavy objects over a distance, and in some cases those situations may be excluded from the gait analysis to avoid skewing the gait analysis.

Figure 3:
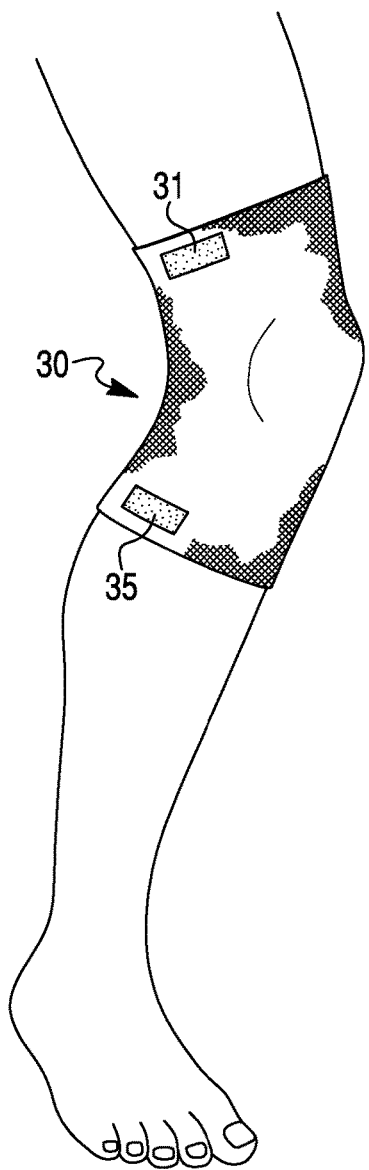
FIG. 3 is a leg sleeve according to an example of the present disclosure.

FIG. 3 illustrates a leg sleeve 30 positioned on a right leg, although the sleeve 30 may alternatively be placed on a left leg. The leg sleeve 30 may include two sensor packages. First sensor package 31 may be positioned on a lateral side of the thigh in an anatomical position, and second sensor package 35 may be positioned on a lateral side of the shank in an anatomical position. Other suitable sensor locations may be used within the principles of the present disclosure, including the medial, anterior, or posterior surfaces of the thigh and shank. First sensor package 31 may be configured to be positioned on a first side of a joint (e.g., the knee), and second sensor package 35 may be configured to be positioned on a second side of the joint.

Figure 4:
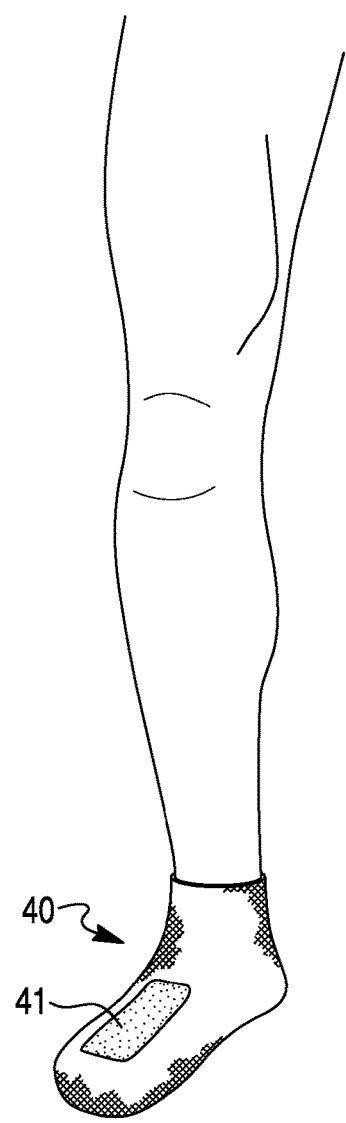
FIG. 4 is a perspective view of a sock according to an example of the present disclosure.
Figure 5:
FIG. 5 is a bottom view of a sock according to an example of the present disclosure.
Figure 6:
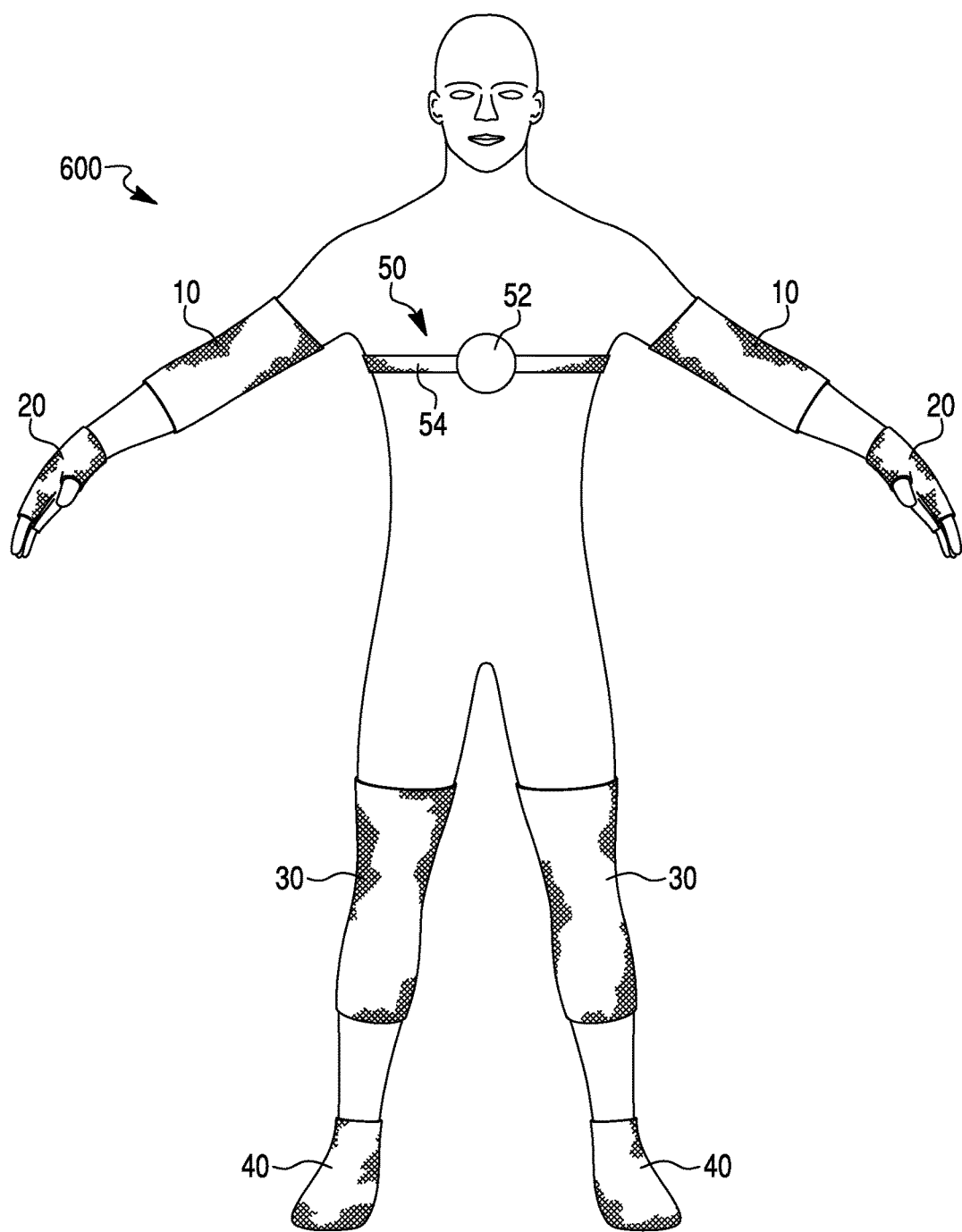
FIG. 6 depicts a user wearing a kit according to an example of the present disclosure.

FIGS. 4 and 5 illustrate a sock 40. With reference to FIG. 4, the sock 40 may include one or more sensor packages 41. A sensor package 41 may be placed on the dorsal side of the foot. Referring to FIG. 5, the sole of the sock may include one or more pressure sensors 24. In this example, one sensor 24 may be placed at the heel, and two sensors 24 may be spaced apart from one another at the ball of a foot. The positions of the sensors on the foot may facilitate the collection of specific data. The different contact points may generate different joint kinetics calculations. The use of multiple sensors 24 may allow for a more nuanced and more accurate analysis than a system that generalizes the foot as one contact point. In one example, the plantar pressure sensors 24 may measure the physical parameters that the right and left foot experience, and the top or dorsal sensor package 41 may measure movement data that the right and left foot experience. In some examples, the socks 40 may utilize a plurality of sensors to achieve full foot mapping to enable orthotics producers to create custom foot beds for people in order to assist them in correcting their gait.

Referring to FIG. 6, a chest piece 50 may include a strap 54 and a hub 52. The strap 54 may include an elastic material and/or may be adjustable. The strap 54 may further include a coupling portion (not shown), such as a snap or clip to allow the user to connect the ends of the strap. The hub 52 may include a sensor package and may be positioned on the ventral side of the user. In other examples, the hub 52 may be positioned on the user's back, or on the user's sides. In some examples, the hub 52 may include more memory than the other sensor packages described herein and may receive data from sensors located on the one or more arm sleeves 10, gloves 20, leg sleeves 30, or socks 40. The hub 52 may transfer the data to a gateway device (e.g., any device which is connected to the Internet, like a phone, desktop computer, laptop, mobile application or web application) and/or a remote server. In another example, chest piece 50 may be a shirt or other garment configured to position a hub 52 adjacent to a user's torso. For example, the chest piece 50 may include a compression shirt with a hub 52 secured to the shirt and configured to be positioned on the user's ventral side.

FIG. 6 illustrates a user wearing a wearable kit 600 that may include, for example, two arm sleeves 10, two gloves 20, two leg sleeves 30, two socks 40, and a chest piece 50. Thus, the kit 600 may be an nine-component kit for biomechanics analysis, motion capture, and/or gait analysis. Kit 600 may include one wireless charging box (not shown) or wired charging protocol that can charge the nine different components of kit 600 simultaneously or independently. In some embodiments, one or more of sleeves 10, gloves 20, leg sleeves 30, socks 40, and/or chest piece 50 may be omitted from kit 600 without departing from the spirit of the present disclosure.

In one example, the kit 600 may include a head piece (not shown). The head piece may include a head band, cap, or other wearable component, along with one or more sensors (e.g., a sensor package or pressure sensor). Similar to other wearable components described herein, the head piece may collect movement and/or force data corresponding to the head.

Figure 11:
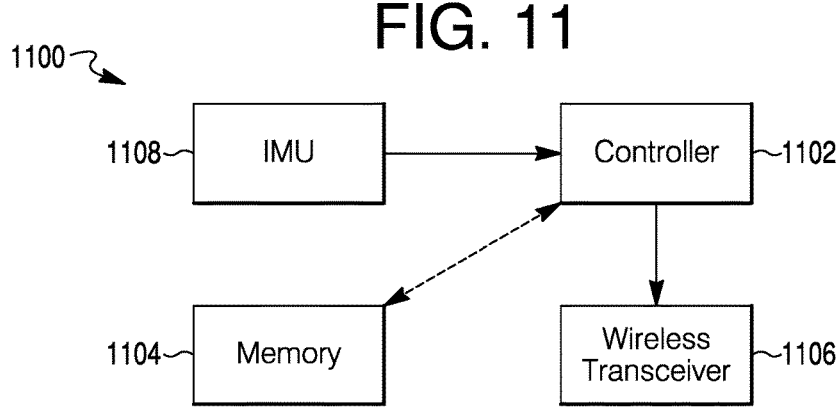
FIG. 11 is a schematic of compression sleeves according to examples of the present disclosure.

A schematic view of the electronic components of a compression sleeve system 1100 is shown in FIG. 11. System 1100 may be substantially similar to the components found in sleeves 10 and 30 described above. System 1100 may include a controller 1102 coupled to a memory module 1104 and a wireless communication module 1106. Controller 1102 also may be coupled to an IMU sensor 1108. In an alternative embodiment, the system 1100 may include more than one IMU sensor. As described above, sensor 1108 may include an accelerometer, a gyroscope, and a magnetometer. The system 1100 may represent an individual arm sleeve 10 or individual leg sleeve 30. A system, such as, e.g., kit 600, may include two arm sleeves 10 and two leg sleeves 30 each having two IMU or orientation sensors, as described in connection with FIGS. 1 and 3.

Figure 13:
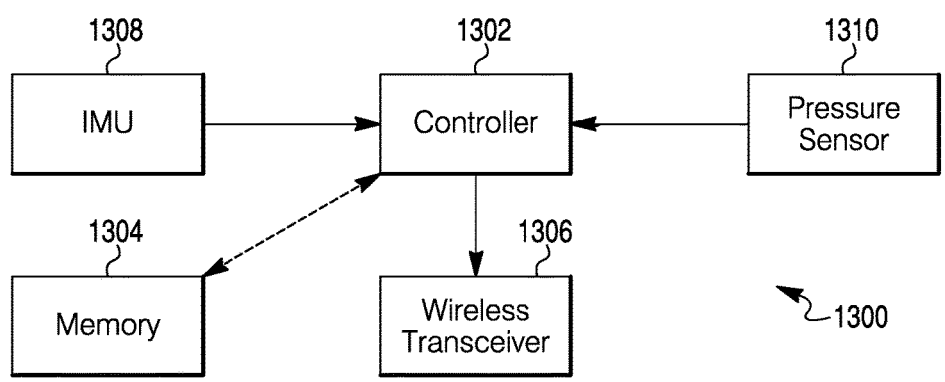
FIG. 13 is a schematic of gloves and socks according to examples of the present disclosure.

A schematic view of the electronic components of a sock or glove system 1300 is shown in FIG. 13. The system 1300 may be used in the glove 20 or the sock 40 described above. System 1300 may include a controller 1302 coupled to a memory module 1304 and a wireless communication module 1306. Controller 1302 also may be coupled to an IMU sensor 1308 and one or more pressure sensors 1310. Sensor 1308 may include an accelerometer, a gyroscope, and a magnetometer, as described above.

Overall System

Figure 9:
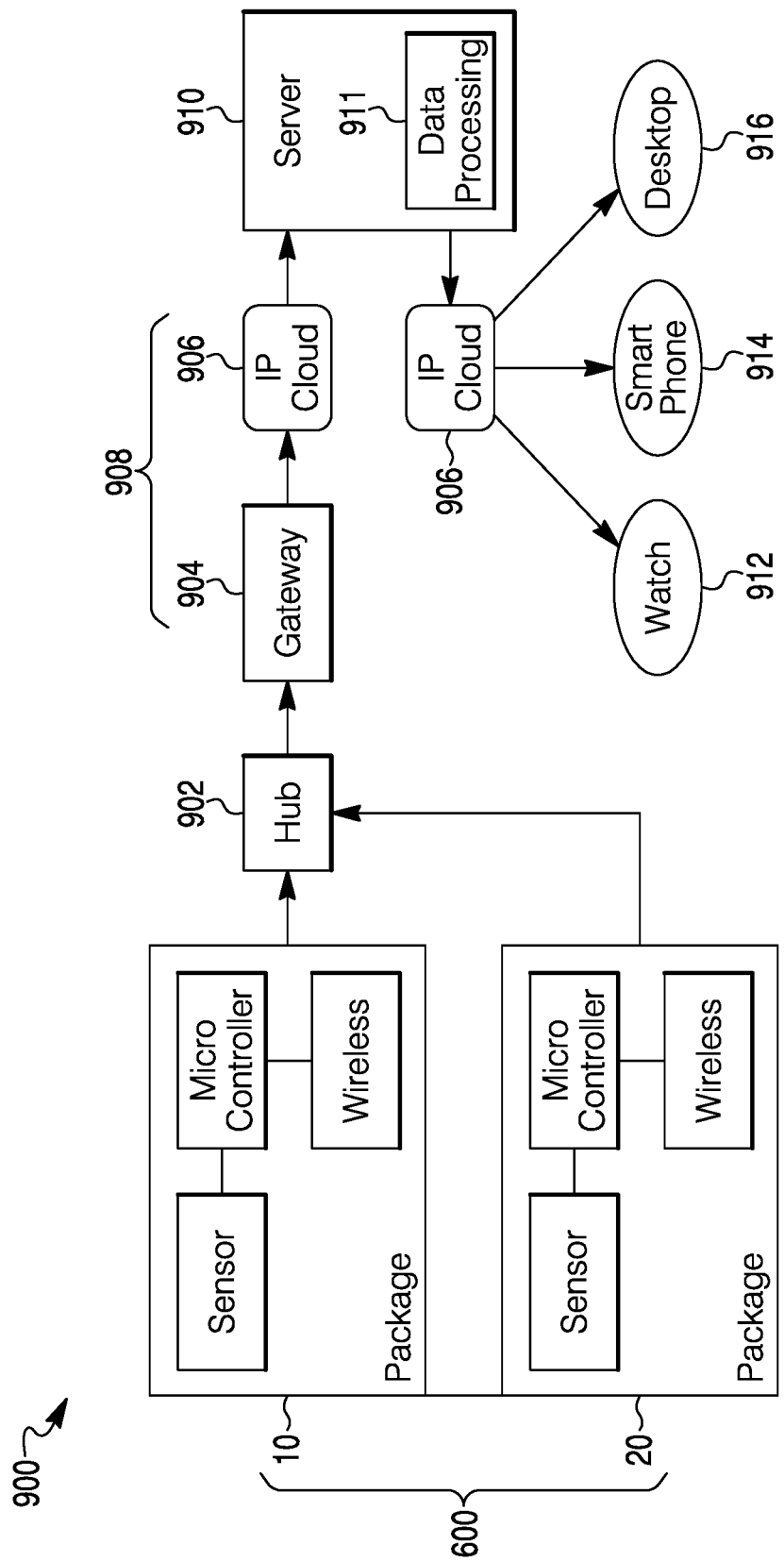
FIGS. 9 and 10 are schematics of systems according to examples of the present disclosure.

FIG. 9 is a schematic illustration of a system 900. Sensors from a kit 600 (from e.g., arm sleeves 10 and gloves 20, shown in FIG. 9) may communicate and transmit sensor data to a hub 902, which may be any suitable electronic device configured to receive the sensor data. In one example, the hub 902 may be located on chest piece 50, like the hub 52 shown in FIG. 6. In one example, the hub 902 may receive information from thirteen different sensor packages, which may include: two on each arm sleeve 10 (four total), one on each glove 20 (two total), two on each leg sleeve 30 (four total), one on each sock 40 (two total), and one on the chest piece 50. Additionally, there may be a fourteenth sensor located on a head piece. The hub 902 may further receive information from pressure sensors on the gloves 20 and socks 40. Hub 902 may transmit the data to a gateway 904 and a cloud 906 that may be part of an electronic network 908 such as, e.g., the Internet. In some embodiments, the transmitted data may be encrypted prior to transmission over the network. For example, in the case of patient data, the data collected at the sensors described herein may be encrypted to, e.g., comply with the Health Insurance Portability and Accountability Act (HIPAA), prior to transmission.

One or more servers 910 may retrieve sensor data from cloud 906, and may analyze and process the sensor data using a data processing module 911. Servers 910 may then send the analyzed (and encrypted) data through cloud 906 to any suitable device such as, e.g., a smart watch 912, a smart phone 914, or a computer 916. Smart watch 912, smart phone 914, and computer 916 may all serve as hub 902 in some examples.

Figure 10:
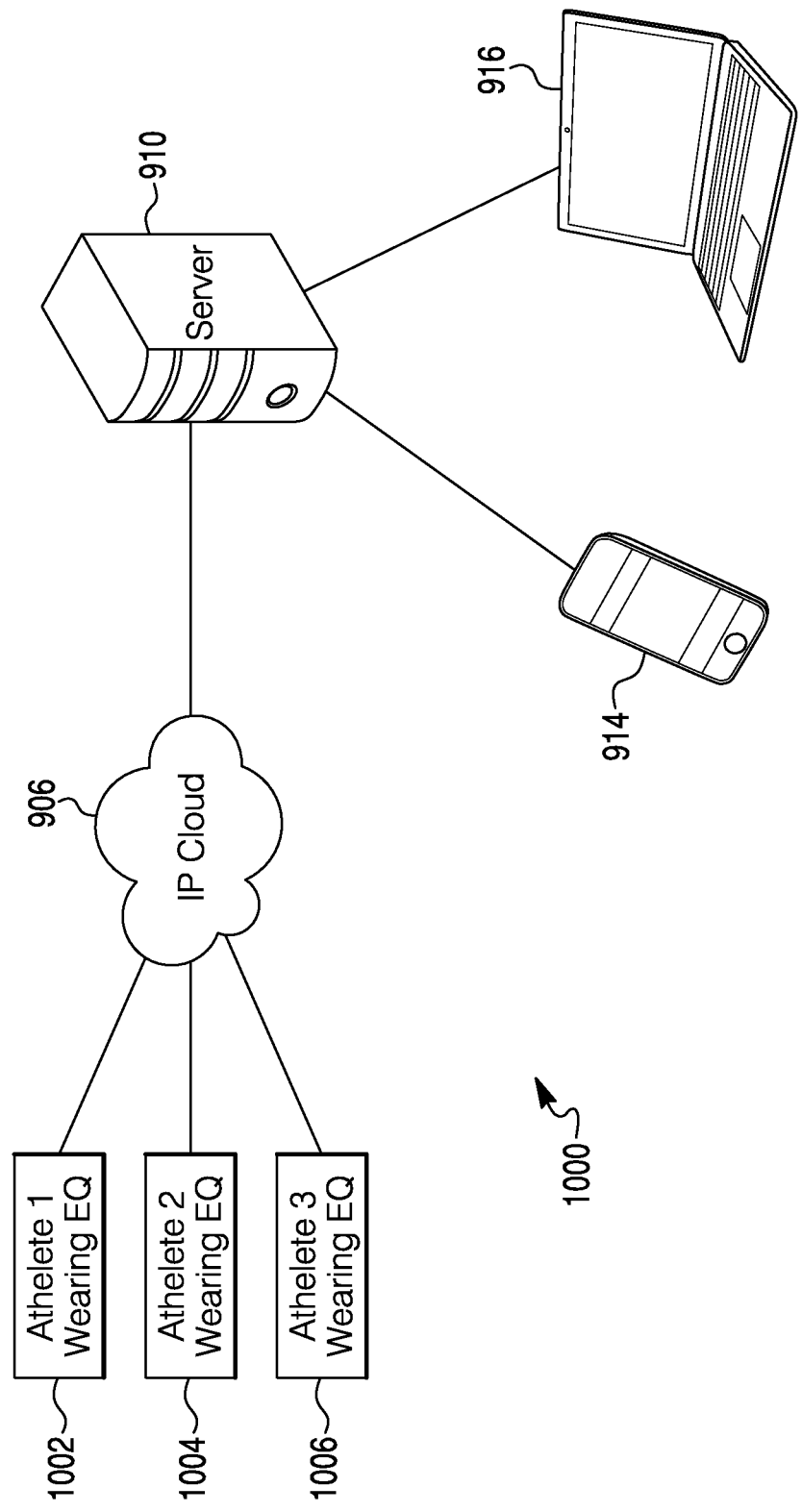

FIG. 10 depicts a system 1000 that is substantially similar to system 900, except that FIG. 10 depicts multiple users 1002, 1004, and 1006 (each having a respective kit 600) who may send data via hub 902 (not shown in FIG. 10) through cloud 906 and to one or more servers 910 for analysis and processing in a similar manner as described in connection with FIG. 9.

Figure 14:
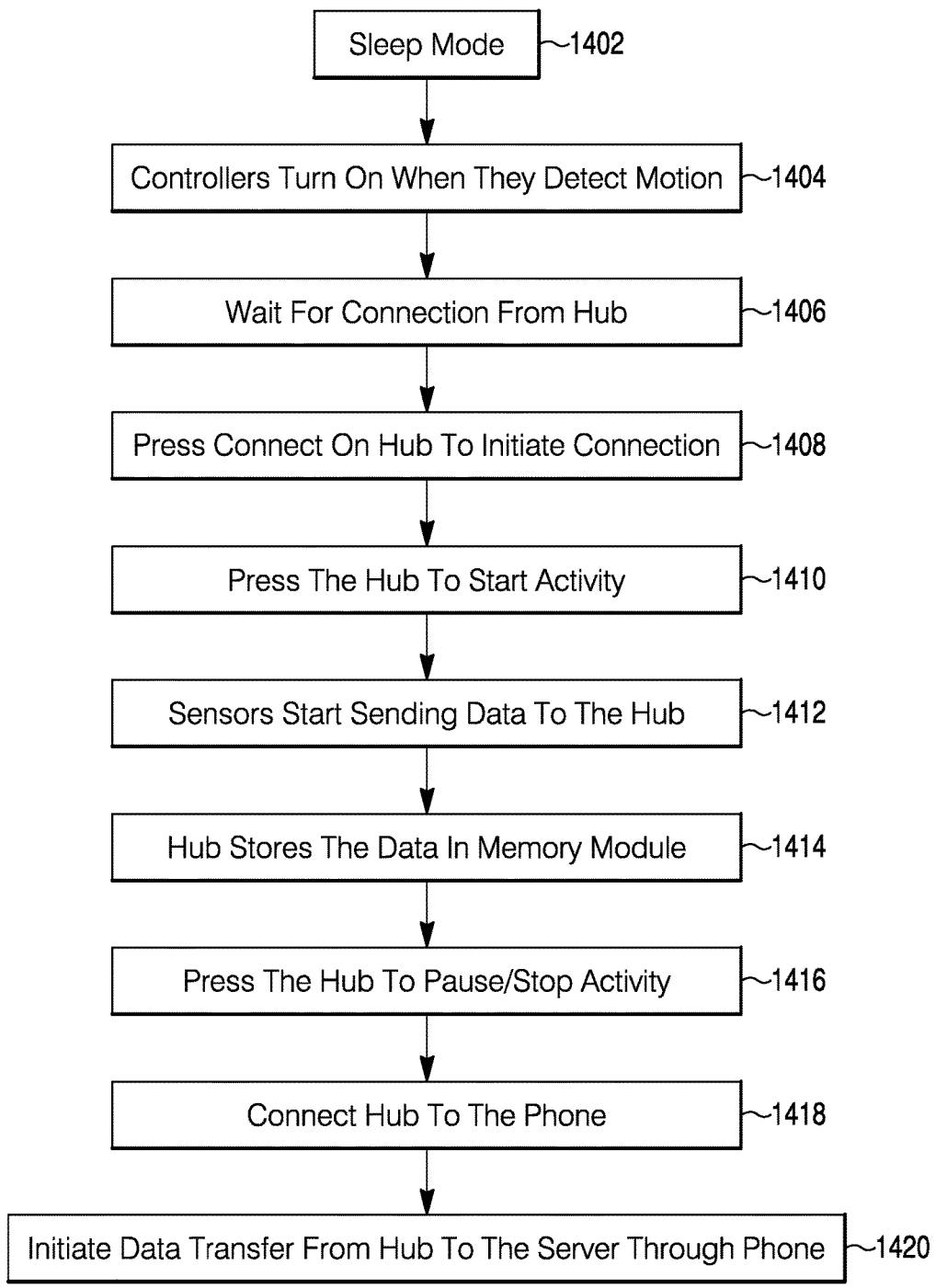
FIG. 14 is a flowchart illustrating the operation of the kit of FIG. 6 according to an example of the present disclosure.

FIG. 14 is a flowchart illustrating the operation of the kit 600 of FIG. 6. The controllers of the sensors may be in a sleep mode when the kit 600 is not being used (step 1402). However, when the user wears the kit 600, the sensors may detect motion and wake up the controllers (step 1404). The controllers may wait on the hub 52 (or 902 in FIG. 9) to initiate connection (step 1406). The user may press a button on the hub 52 to initiate the connection with the other controllers (step 1408) and/or when the user begins an activity (step 1410). All of the sensors may then start sending data to the hub 52 (step 1412). The hub 52 may store the data on its memory module (step 1414). When the user stops the activity, the user may press the button on the hub 52 again (step 1416). In one example, the user may connect the hub 52 to a phone or other gateway device (step 1418). The transfer of data may be initiated from the hub 52 to the server, via the phone or other gateway device (step 1420).

Analysis

The data collected from the various sensors described above may be stored onto a memory chip, which may then upload, via a wireless or wired connection, the collected data to one or more servers when, for example, the sensor is in close range of a gateway device (e.g., any device which is connected to the Internet, like a phone, desktop computer, laptop, mobile application or web application). Alternatively, the collected data may be automatically transmitted to one or more remote servers without being stored in a memory chip local to the sensor and/or without the use of a gateway device. In such embodiments, the sensors may be operatively coupled to, e.g., a cellular, GPS, or other long range transceiver. The one or more servers may include an application running on a remote system connected via an internet protocol, or an application running on a mobile phone (iPhone, Android) or desktop computer.

The collected but raw data from the sensors may be processed by the one or more servers and uploaded back to the gateway device, which may give feedback on the user's bio-mechanical activity to the user or to other professionals. This feedback may be useful to understand the functionality of the subject utilizing the devices, which could pertain to historical or current injuries and performance. The feedback may be accessed in real time (post-processing) and globally via a smart device, such as, e.g., Apple's iPhone® or Watch®. The gateway device that receives the processed data from the one or more servers and displays the feedback to the user does not need to be the same gateway device that facilitates uploading of the data to the remote server. In yet another embodiment, the collected data may be transmitted from multiple sensors to a hub worn by the user. The hub may then transmit the data to one or more servers (with or without using a gateway device), as described above.

In some examples, partial calculations and inferences may be drawn before data is sent to the servers. For example, in those systems that sync sensors via a smartphone or desktop, some basic standard information about the activity may be displayed to the user while an algorithm analyzes the collected data. In some examples, this displayed data may include basic details such as, e.g., elapsed time of the activity, distance travelled, calories burned, activity score (if any), number of steps taken, or the like.

The processors described herein (e.g., processor 74 within sensor packages) may be programmed with an algorithm that collects data from the sensors and stores the collected data onto a memory chip (e.g., memory 76) operatively coupled to a wireless transmitter. When a particular activity finishes (or in real-time during the activity), the wireless transmitters (e.g., within processor 74) of the present disclosure may connect to a gateway device to upload the data onto a server connected to a network, such as the Internet. On the server, data may be analyzed and processed to give various gait, bio-mechanical data, and motion capture data.

IMU or orientation sensors may collect data related to angles (e.g., degrees), rate of change of angles (e.g., degrees/sec), linear acceleration (e.g., m/s2), and respective angular velocities (e.g., degrees/sec) at various locations. Changes in these values over time at a given location may indicate muscle fatigue (e.g., mechanical muscle fatigue). These values may be collected in two or more dimensions (e.g., in three-dimensional space) so that a biomechanical analysis may be performed in all planes rather than only in a frame of translation. The pressure sensors 24 may utilize piezo-electric concepts and may provide a voltage (mV) output depending on the force applied. This may be a resultant force that an algorithm may analyze, and subsequently break down into x, y, and z directional components in order to conduct a two or more dimensional (e.g., a three-dimensional) biomechanical analysis.

The processed data may then be uploaded back to the gateway device, which will give feedback on the user's bio-mechanical activity that may be displayed to the user on any smart device and/or PC. The user may have access to the data in real-time (e.g., post-processing), proximally, or remotely. Through the user's account, the user can access his/her previous activities and plot progress. The user may send this data to, e.g., a specialist or expert anywhere in the world (e.g., physical therapist, orthopedics, etc.) to get a more thorough and full analysis and feedback.

In some examples, fatigue over time may be estimated and/or determined for a particular activity by mapping rate of change of angles of the various sensors. Similarly, fatigue may be estimated or predicted by mapping a change in acceleration or deviation from an ideal movement path or trajectory.

Examples of the present disclosure may measure and analyze full body biomechanics and gait analysis on-the-go, including biomechanics analysis of multiple varieties of activities in two or more dimensions. Examples of the present disclosure may facilitate remote consultation with doctors, therapists and experts by providing comprehensive analysis reports.

Examples of the present disclosure may facilitate approximating localized calories burned calculated specifically for different kinds of activities.

Examples of the present disclosure may be configured to recognize certain activities based on input from the sensors. For example, analyzing patterns of movement with respect to orientation of the entire body and specific limbs in two or more dimensions may allow for the recognition of the activity the user is performing. Data from the sensors (e.g., accelerometer, gyroscope, and magnetometer) with respect to the earth may be compared to a database of data known to relate to performed activities. For example, collected data from sensors of sock 40 may be compared to data previously collected from previous users wearing a sock 40 to help controllers of the present disclosure recognize that a certain type of exercise or activity occurred. For example, when a user is swimming, data collected from the various sensors may be compared to the database of known data, and an algorithm may determine that the collected data is representative of someone that is swimming. Once a recognition is made that a user is performing a particular activity, a more tailored and nuanced analysis may be performed and activity-specific information can be relayed to the user.

The sensors (e.g., IMU sensors, orientation sensors) may collect acceleration, angular velocity and the orientation of the body with respect to the earth's magnetic field. The pressure sensors may collect the points of contact of the foot or the hand with an external object (e.g., the ground, weights). A controller may collect all of these inputs, apply adequate filters, and provide outputs. One output may be ground reaction forces. Another output may include forces acting on various joints in the x, y, and z directions. The joints analyzed may be the ankle, knee, hip, wrist, elbow and shoulder on right and left sides, each joint being associated with a sensor responsible for conducting analysis specific to its associated joint. Another output may be the torques acting on various joints in the x, y, and z directions. Another output may be body portion orientation (e.g., arm, forearm, thigh, shank, foot, torso, etc.), which may be calculated in a local frame of reference, and/or total body orientation in two or more dimensions, which may be calculated in a global frame of reference. Another output may be whether the user is experiencing fatigue over time, although in some examples, the system may not measure muscle activity, any muscular signals, or lactic acid build up in the blood stream. Instead, pure mechanical changes with respect to time may be used to see certain muscular areas around respective joints and analyze which ones are mechanically slowing down or speeding up. Another output may be horizontal and/or vertical impulses generated in the x, y, and z directions.

Normally only one frame may be analyzed. The analyzed frame may be the one in which the body translates and where maximum movement occurs. However, other planes in two or more dimensional space that have less movement may still be analyzed, and in fact, may be important to help understand and correct body mechanics and joint kinetics. Another output may include distance covered (e.g., an approximate estimation with or without GPS). This may be calculated based on an activity recognized and steps or strokes measured. Another output may include calories burned in a localized area. Another output may be velocity and acceleration for users interested in knowing the pace at which they are performing an activity.

The data collected by systems of the present disclosure may be able to help determine the rate at which each segment of the body changes angle with respect to a reference plane over time. For example, analysis systems may determine the speed of different muscle movements, such as, e.g., shoulder flexion and extension, elbow flexion and extension, wrist extension, flexion, supination, pronation and similarly hip flexion and extension, knee flexion and extension, ankle extension flexion, inversion and eversion. These movements may be caused by particular agonist and antagonist muscle groups. Systems of the present disclosure may be able to measure and/or determine the rate at which the above movements are caused and may be able to determine the muscle groups responsible for speeding up or slowing down such activities. These determinations may be used to estimate which muscle group or groups are slowing down or fatiguing over the course of a measured activity.

Figure 12:
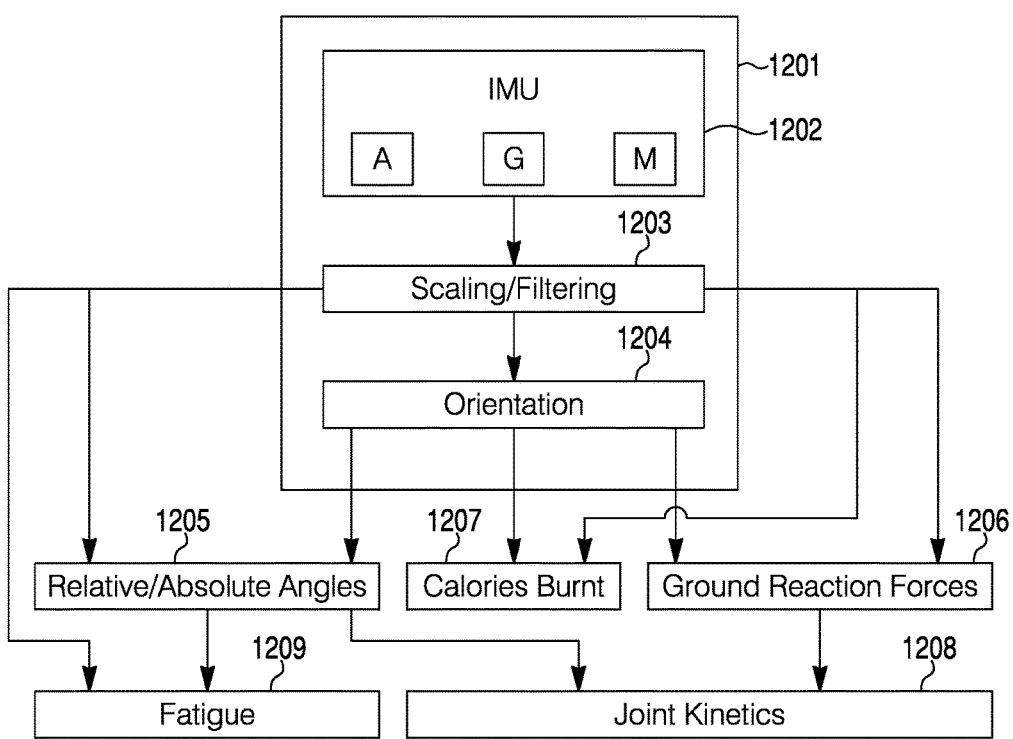
FIG. 12 is a flow chart of a method for analyzing movement data from sensors according to an example of the present disclosure.

FIG. 12 depicts an exemplary method of analyzing data collected from the kit 600 of FIG. 6 and its various sensor packages (e.g., IMU sensors), including calculating the orientation of body portions in two or more dimensions. For example, information from sensor package 11 (see FIG. 1) may be used to calculate the orientation of the upper arm in two or more dimension(s), and information from sensor 41 on the foot (FIG. 4) may be used to calculate the orientation of the foot. A pre-processing module 1201 may include pre-processing steps. Sensor package 1202 may be similar to the package 70 of FIG. 7 (and similar to the sensor packages described in connection with the various devices of kit 600 described herein) and may provide raw accelerometer/gyroscope/magnetometer values. The scaling portion of step 1203 may set a range for the raw values, and the filtering portion may include noise removal (e.g., a moving average filter), drift compensation (Kalman filter), signal decomposition (low pass/high pass filter), etc. The values from step 1203 may be used to calculate the global orientation of the sensor package 1202 (step 1204); furthermore, the scaled and/or filtered values may be used in the computation of different parameters like ground reaction force (GRF), fatigue, etc. Local orientation data from each sensor package (s) of kit 600 (e.g., including 1-13, 14, or more sensor packages) may be used to calculate the orientation of each corresponding body segment in two or more dimension(s).

Step 1205 may include calculating the relative/absolute angles of the body segments. Inputs to this calculation may include the values from steps 1203 and/or 1204. The orientation obtained by each sensor may be converted from a global orientation to a local orientation. The local orientation system may be based on a few sample user activities. For example, the user may be asked to sit or stand for a few seconds, or to do other basic movements and/or exercises. Additionally or alternatively, the local coordinate system may be established based on the user's physical characteristics, as described in connection with FIGS. 16A and 16B.

The local coordinate system then may be used to compute the absolute/relative angle(s) in two or more dimension(s).

Step 1206 may include computing ground reaction forces using the data from steps 1203, 1204, and pressure sensors 24 in the gloves 20 and socks 40. Step 1206 may utilize the principles of impulse-momentum change theorem. The human body may be modeled as a collection of connected body segments. In one example, if the kit 600 includes multiple (e.g., thirteen) sensors, the equation used to compute ground reaction forces may be: $\Sigma m_i \times a_i$, where mass and acceleration correspond to the $i^{th}$ body segment. Pressure sensors 24 may be used to identify contact points of the hands and feet. In one example, the acceleration of a segment (e.g., the forearm), the orientation of the segment, and its mass and length may be used to generate values that pertain to the forces being exerted on or experienced by the segment in two or more dimension(s). The value set may include a force and a direction along which the force is being experienced.

Figure 17:
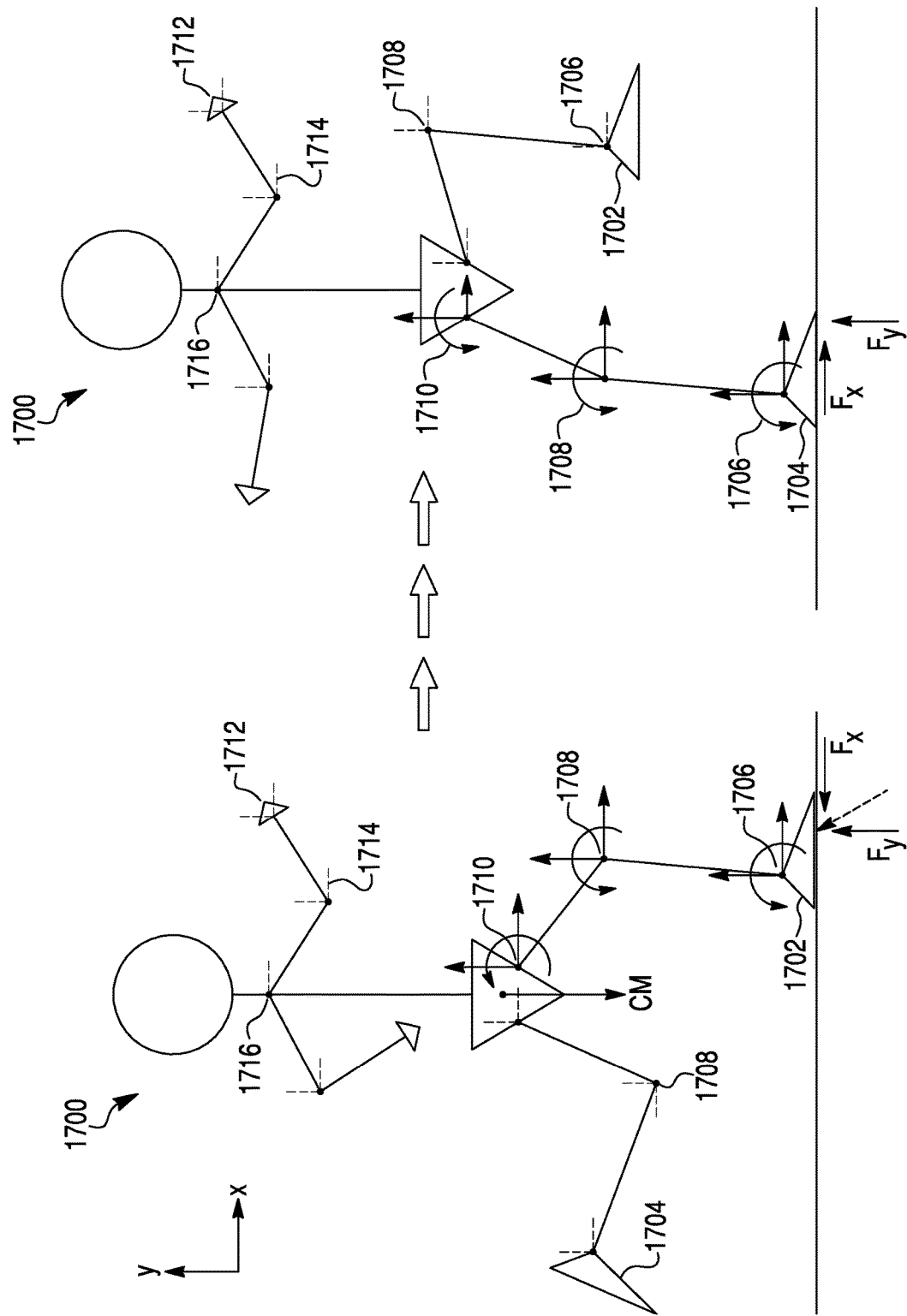
FIG. 17 is a representation of an athlete according to an example of the present disclosure.

Step 1208 may include using values from steps 1205 and 1206 to calculate joint kinetics. Referring to FIG. 17, an illustration of an athlete 1700 is shown at two different times of a running motion. In FIG. 17A, foot 1702 may be in contact with the ground, and ground reaction forces in multiple planes may be calculated while foot 1702 is in contact with the ground. In FIG. 17B, foot 1704 may be in contact with the ground and a similar analysis may be conducted. Thus, previously calculated ground reaction forces (step 1206) and external forces acting on the body at different contact points may be simultaneously integrated with the orientation of the body in two or more dimensional space to provide the joint kinetics in step 1208 (forces and torques) that the ankles 1706, knees 1708, hips 1710, wrists 1712, elbows 1714, and shoulders 1716 experience in X-, Y- and/or Z-planes. Devices and methods of the present disclosure may eliminate the need for cameras used by certain prior art systems. To find a problem or the true cause behind a problem, a comprehensive bio-mechanical analysis may be conducted which, in contrast to certain prior art systems, may involve tracking human activity and posture for the entirety of a day rather than for 15 to 20 minutes in a lab.

The estimation of local calorie burn (step 1207) may be determined based upon a determination of the muscle groups responsible for a particular activity, and vice versa. Steps 1203 and 1204 may be used to make this data more efficient. The filtered data and the orientation data from steps 1203 and 1204, respectively, can then be factored to identify a particular group of muscles that are primarily responsible for maximum or minimum caloric expenditure. Information related to calories burned can be very beneficial for the health, wellness, fitness and weight loss industries.

Mechanical fatigue (step 1209) in some examples may be determined by detecting changes in accelerometer data during step 1203, orientation data in step 1204, and relative/absolute angles determined in step 1205. A segment or a joint may be analyzed based on changes in these parameters to determine the localized mechanical fatigue. In one example, the center of mass and the total mass of the arm and forearm for the arm sleeve 10, and of the thigh and shank for the leg sleeve 30, may be integrated to estimate muscle fatigue in various locations of the body. For example, the data collected by the arm sleeve 10 can be used to estimate the fatigue in the muscle groups that are responsible for shoulder flexion and shoulder extension, and elbow flexion and elbow extension. Further, the data collected by the leg sleeve 30 may be used to estimate the fatigue in the muscle groups responsible for hip flexion and hip extension, as well as knee flexion and knee extension.

In one example, a kit 600 (see FIG. 6) may include thirteen accelerometers, thirteen gyroscopes, and thirteen magnetometers (e.g., within sensor packages), that may provide the orientation of body segments and/or total body orientation in three-dimensional space. The data from these components may be processed as described in connection with FIG. 12. For example, the data from the thirteen accelerometers may be passed through a filter in step 1203. Additionally, the data from the accelerometers, magnetometers, and gyroscopes from each of the sensors of the kit 600 (e.g., the thirteen IMU sensors) may help provide an orientation of the thirteen sensors in step 1204. The filtered acceleration data and the orientation data may be utilized to calculate acceleration of each of the thirteen sensor points in the x, y, and z directions. The acceleration data may be used in conjunction with the lengths and masses of different body segments to calculate the forces acting on each sensor point in the x, y, and z directions. These calculations may be used to determine the forces acting on the center of mass of the entire body, which may, in conjunction with data from the pressure sensors 24 in the socks 40 and gloves 20 of the kit 600, be used to determine ground reaction forces (step 1206) and orientation of the entire body.

The individual values of these sensors may be passed through a filter to give acceleration of each of thirteen segments of the body in X-, Y-, and Z-planes. These accelerations along with the initial calibration of each segment length, total mass, and center of mass may be used to calculate the total body center of mass and the forces in X-, Y- and Z-planes that the total body center of mass experiences. After evaluating the overall forces in three-dimensional space that the center of mass of the total body experiences, the algorithm then may (simultaneously or subsequently) integrate with the values of the pressure sensors and sensor packages in the gloves and the socks to get the ground reaction forces, points of contact of the hands/feet, and orientations of the hands/feet in X-, Y- and Z-planes. Systems of the present disclosure may factor in values from all the sensors to determine the acceleration in x, y, and z directions experienced by the body center of mass, which will then be used to find the direction and magnitude of the external force acting on the body at any point of contact.

As described above, information from sensors (e.g., IMU sensors) may be used to calculate the orientation of the body segments and total body orientation in two or more dimensional space and to estimate muscle fatigue. For example, one strategically-placed sensor 23 may provide orientation data for the palm to estimate the fatigue in muscle groups responsible for wrist flexion and wrist extension, radial deviation and ulnar deviation, pronation and supination using data collected from the wrist, forearm, and hand. In some examples, the systems may not point to a particular muscle but instead may provide a whole-body metric. Similarly, one strategically-placed sensor 41 on each sock may allow the algorithm to estimate the fatigue caused by muscle groups responsible for ankle plantar flexion and dorsiflexion, inversion and eversion.

The strategically-placed pressure sensors 24 of the socks 40 may be configured to measure the contact points during multiple phases of the gait cycle, including the gait contact phase which begins with a heel strike on the lateral border of the calcaneus, the mid-distance phase that converts the foot from a mobile adaptor into a lever, during which the tibia externally rotates and the foot supinates at the subtalar joint preparing the foot for the propulsion phase, and the propulsion phase that begins at heel lift. In some examples, systems of the present disclosure may factor what phase the body is making contact with the ground because the point of application of the ground reaction forces (step 1206), and the different joints, may be important parameters for various joint kinetics (step 1208) calculations. Different phases may change the point of application of the ground reaction forces, which may change the magnitude and direction of the joint forces and the joint torques.

Figure 15:
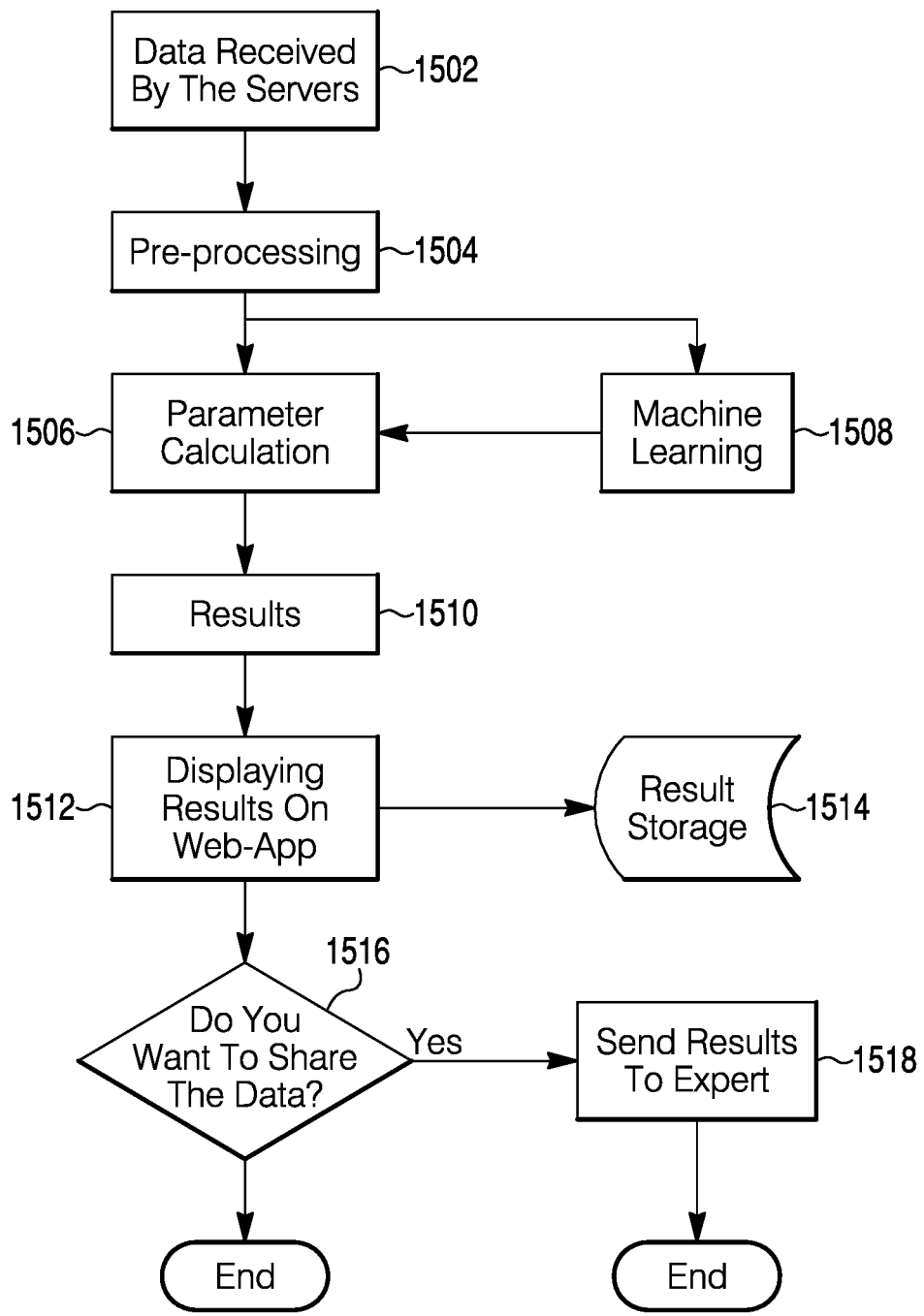
FIG. 15 is a flowchart illustrating analyzing sensor data and providing feedback according to an example of the present disclosure.

FIG. 15 illustrates exemplary steps for processing sensor data. The data may be received by the servers from the sensors (step 1502). The data may then be sent to the pre-processing module (step 1504). This may be the pre-processing module 1201 of FIG. 12, and the data may be scaled and filtered as described in connection with FIG. 12. The pre-processing module may further receive information related to the user's profile, such as age, height, weight, and other information requested during user registration. Various parameters may be calculated in step 1506, as described in connection with FIG. 12 (e.g., relative/absolute angles, calories burned, ground reaction forces, fatigue, and joint kinetics). Machine learning may be used to assist in calculation of the parameters (step 1508). The results may be determined (step 1510), and they may be displayed on a web-app (step 1512). The results may be stored in a database (step 1514). If the user wants to share data (step 1516), the data may be sent to an expert for review (step 1518).

Figure 16A:
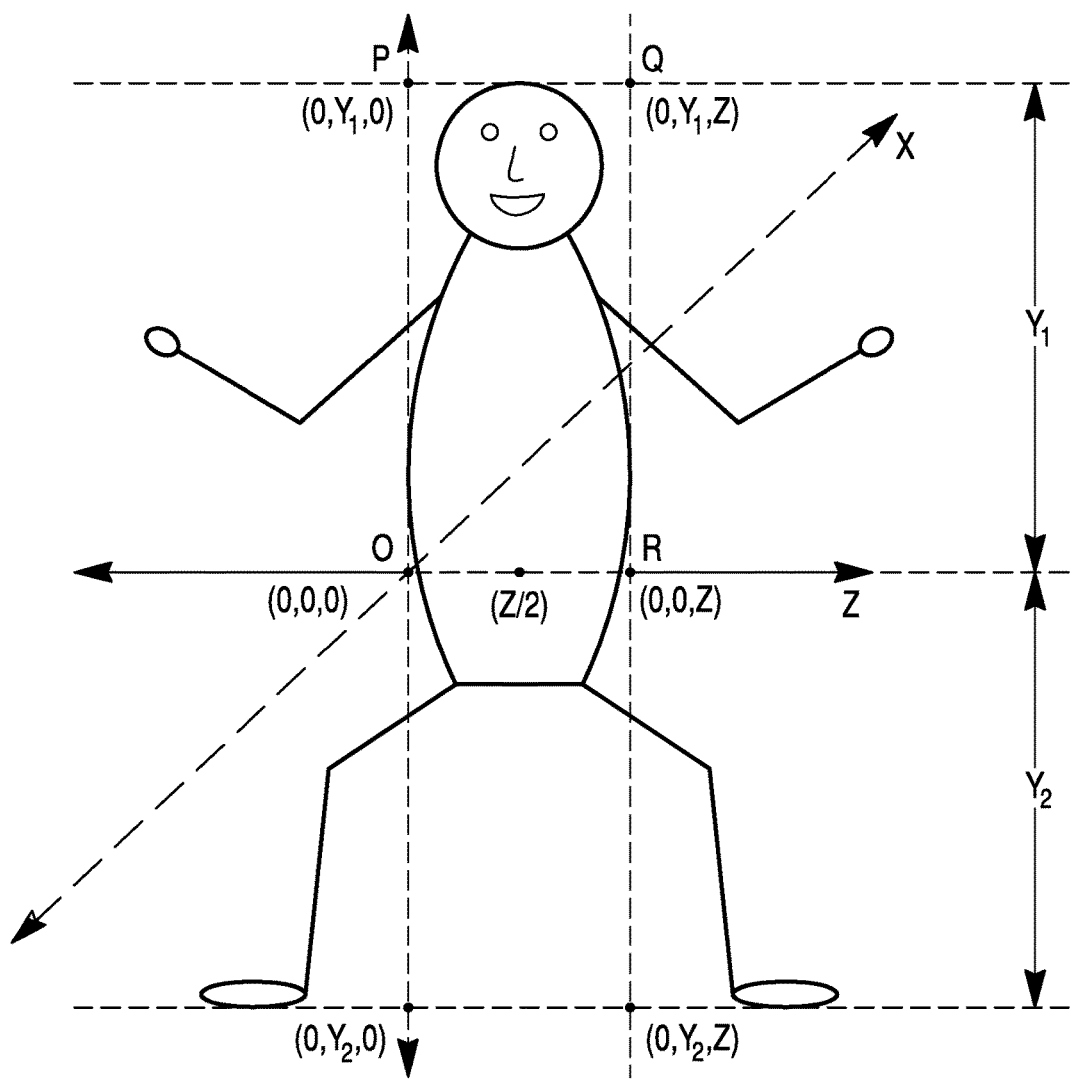
FIGS. 16A and 16B illustrate orientation calculations according to an example of the present disclosure.
Figure 16B:
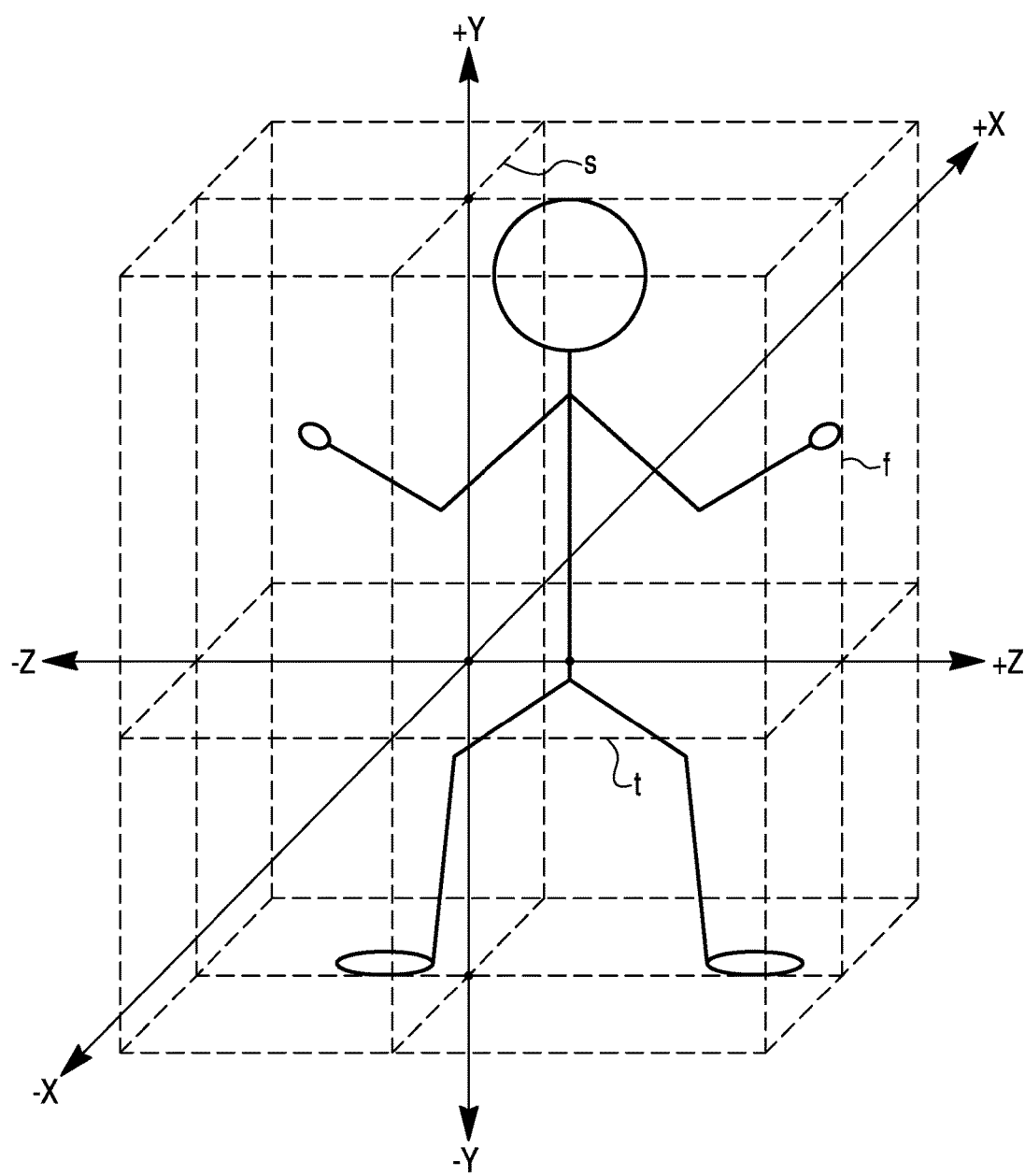

FIGS. 16A and 16B illustrate a method for calculating the orientation of segments of the body, as described in connection with step 1204 of FIG. 12. The data from the various sensors of kit 600 (e.g, acceleration, angular acceleration, magnetic field and points of contact) may be used to compute the orientation of each local segment of the body in three-dimensional spaces. These segment orientations then may be used to determine absolute and relative joint angles (FIG. 12, step 1205), which in turn may be used for the calculation of joint kinetics (e.g., joint forces and joint torques) (FIG. 12, step 1208).

A sensor fusion algorithm may be used to compute the local and/or the global orientation of the given segment. The orientation may be calculated in two or more anatomical planes—sagittal, frontal, and transverse planes.

In one example, a body coordinate system (BCS) may be established without requiring the user to perform any activity. The BCS may be established using the user's input data in the form of his/her height, waist size (e.g., a circumference, a length/width), and shoe size. The BCS may be fixed by setting up planes and axes defining a user-specific coordinate system.

First, a frontal plane f may be established using data from the user. Referring to FIG. 16A, the right side of the waist may be fixed as the origin O. Point R may be a distance "z" from the origin, and point P may be a distance $Y_1$ from the origin. Using any three points within the plane, the frontal plane may be defined as: $a_f x + b_f y + c_f z + d_f = 0$. Referring to FIG. 16B, a plane parallel to the sagittal plane s (referred to as sagittal plane s) that passes through the origin may be defined as: $a_s x + b_s y + c_s z + d_s = 0$, and a transverse plane t that it is both perpendicular to the frontal plane f and the sagittal plane s and passes through the origin may be defined as: $a_t x + b_t y + c_t z + d_t = 0$.

Referring to FIG. 16B, the intersection of frontal plane f and transverse plane t provides the z-axis of the BCS, the intersection of frontal plane f and sagittal plane s provides the y-axis of the BCS, and the intersection of sagittal plane s and transverse plane t provides the x-axis of BCS. Thus, the BCS is now defined. The equations for each plane may then be solved to compute the orientation of each local segment of the user's body.

User Interfaces

Figure 8A:
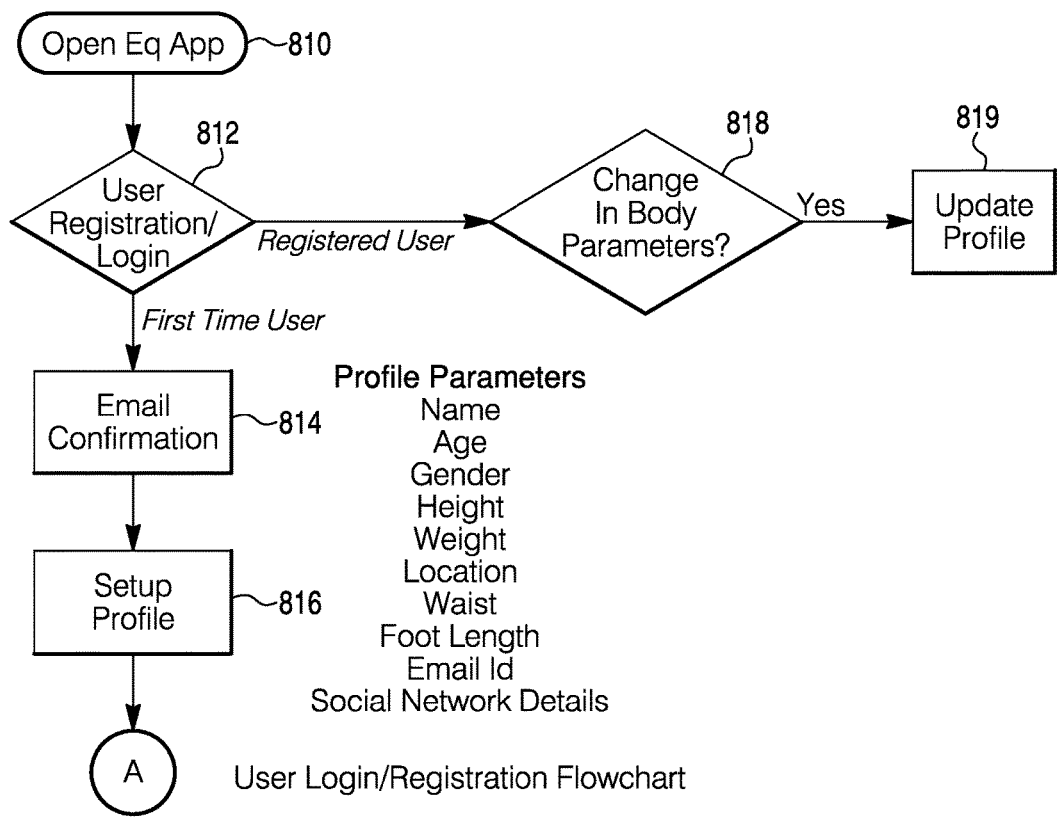
FIG. 8A illustrates a method for user login and registration according to an example of the present disclosure.

FIG. 8A illustrates a process for user login and/or registration. In step 810, a user may open a mobile or web application (an "app"). The user may then register if the user is a first time user or login if the user is a registered user (step 812). If the user is a first time user, the user may receive an email confirmation (step 814). Once the user confirms his/her email, the user may then set up his/her profile (step 816). If the user is already a registered user, the user interface may ask the user if there has been a change in body parameters (step 818). If so, the user may update his/her profile (step 819). The profile parameters may include, for example, name, age, gender, height, weight, location, waist size, foot length, email ID, social network details, etc.

Figure 8B:
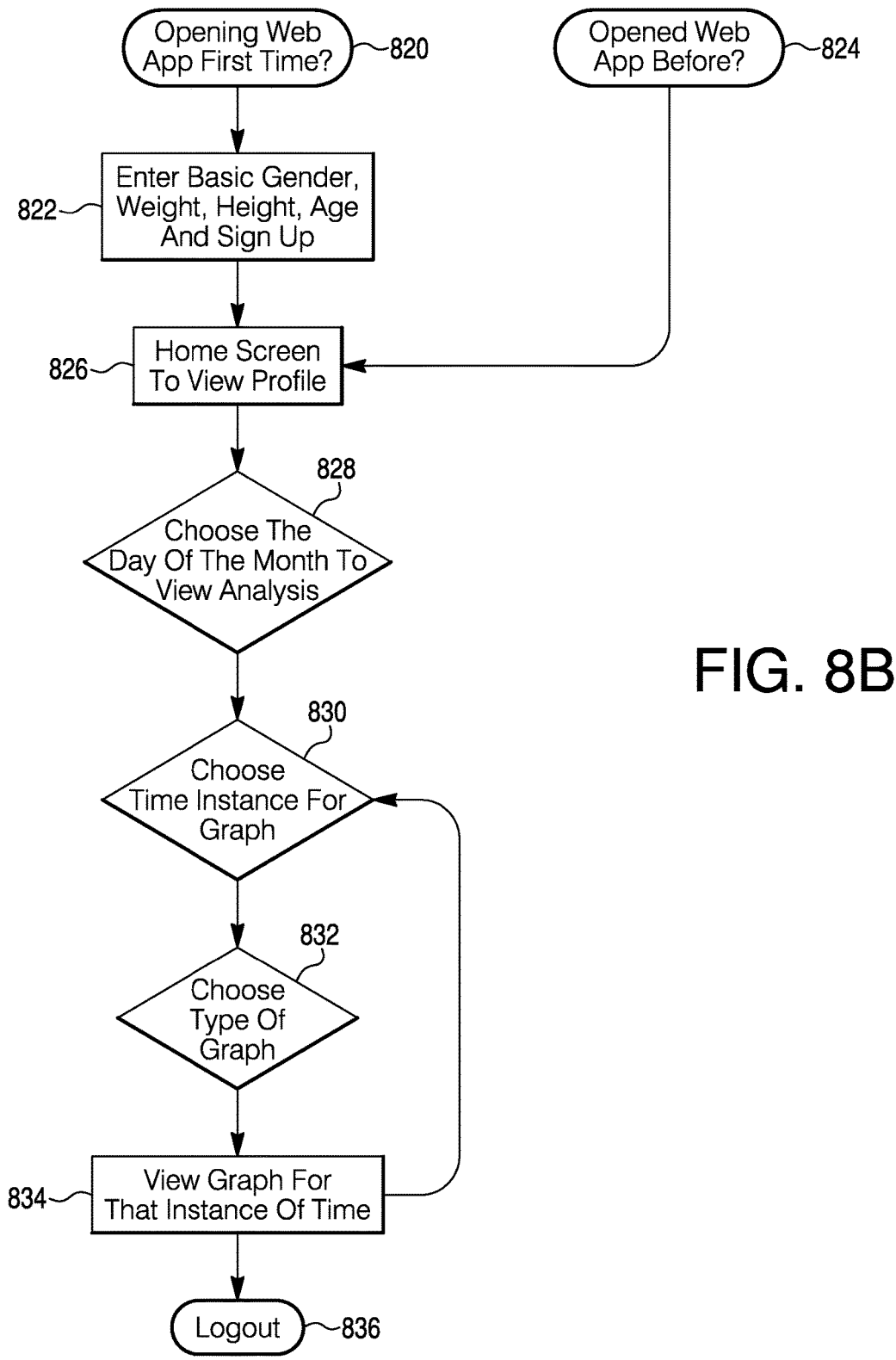
FIG. 8B illustrates a method for providing user feedback according to an example of the present disclosure.

FIG. 8B illustrates a process for a user to obtain feedback from an analysis of data collected by the kit 600. If the user is opening the app for the first time (step 820), the user may be prompted to enter in basic information, such as gender, weight, height, and age to sign up (step 822). The user may then be routed to the home page to see his/her profile (step 826). If the user has opened the app before (step 824), the user may be routed directly to his/her home screen. In steps 828 and 830, the user may choose a time interval to view an analysis. The time interval may be include components such as a day of the month (step 828) and a specific time instance (step 830). The time instance may be, for example, the duration of a certain activity. In step 832, the user may choose a type of graph, and the user may view the graph in step 834. The user may logout in step 836.

Figure 8C:
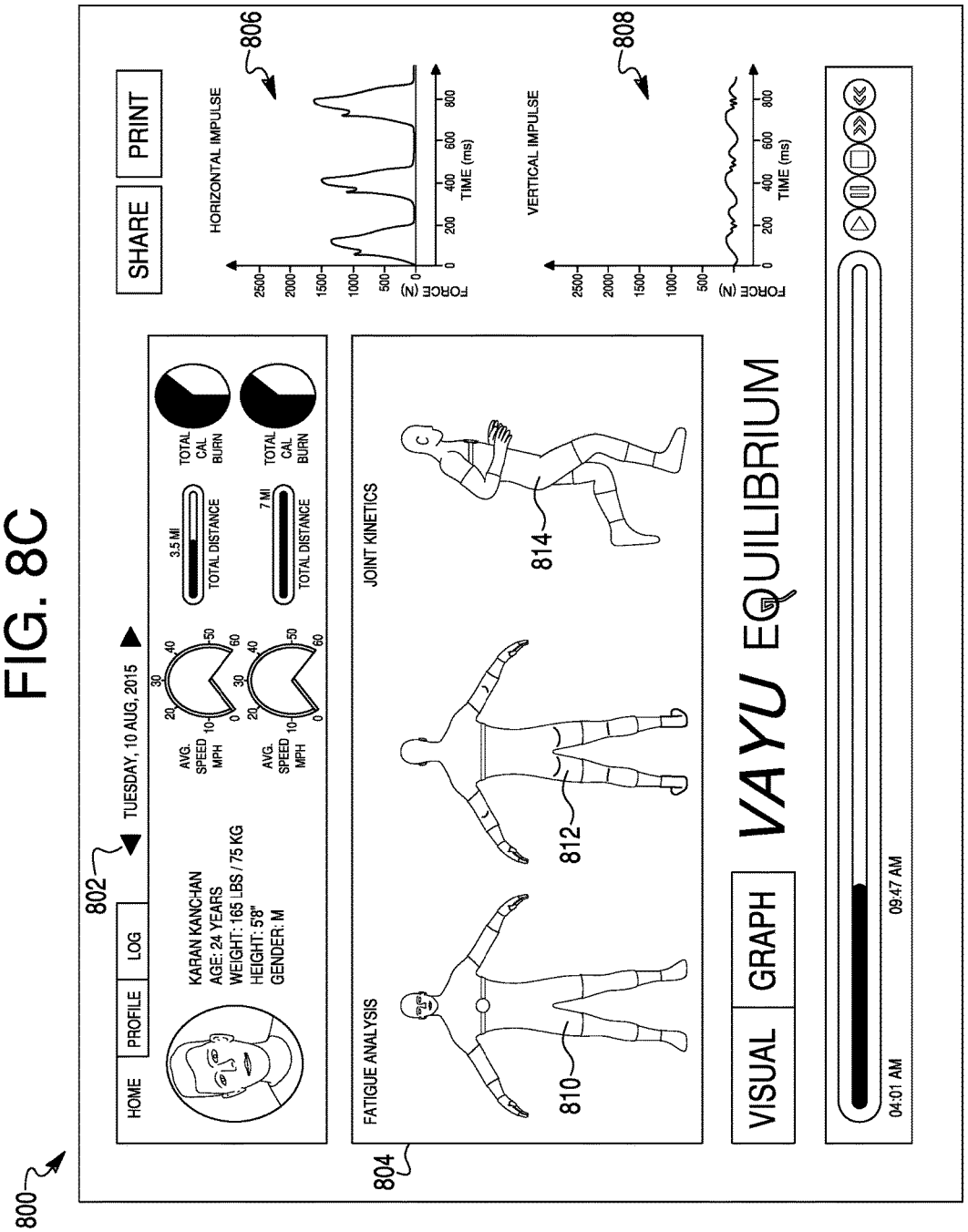
FIG. 8C is a user interface according to an example of the present disclosure.

An exemplary user interface 800 is shown in FIG. 8C. The user interface may be part of a web-based application providing graphical and visual biomechanical analysis, gait analysis, and motion capture feedback. The user interface 800 also may be configured to provide analysis reports. As discussed above, the collected data may be analyzed to provide feedback on the entire body's biomechanics which is represented visually and graphically on user interface 800 and can be viewed using any smart device, such as, e.g., an iPHONE®, iPAD®, computer, or similar device. Through the user's account, he/she can access their previous data and feedback via a date selector tab 802, and plot their progress.

The biomechanical feedback may give graphical and visual representation of analysis of the information collected by the kit 600. For example, information that may be provided to the user via the user interface 800 includes: body joint forces and torques (e.g., in body representation area 804), ground reaction forces, horizontal and vertical impulses (e.g., charts 806 and 808), body orientation, fatigue for various segments of the body, body acceleration, body velocity, distance covered, and calories burned (accounting for different physical activities and muscle groups responsible). The representations may be made in two or more dimensional space using, e.g., a wireframe or solid graphical representation. User account-based data may be made accessible, with permission, to doctors, or therapists/experts around the world, in order to create a wireless/virtual consultation beyond geographic constraints.

The graphs providing feedback (e.g., on the right side of interface 800) may correspond to a model of the user in the body representation area 804. For example, if the user selects to view joint forces in a graph and selects a particular joint, all of the forces acting on that joint may appear next to that joint in the body representation area 804, and the joint may be highlighted in the body representation area 804. For each type of graph, the user may select specific information to be viewed. For example, the user may select to view ground reaction force information in one or more of the X, Y, and Z directions.

Impulses may be useful to professional athletes to understand. For example, a runner may desire more horizontal impulse and less vertical impulse, while a high jumper may desire opposite metrics (low horizontal impulse and high vertical impulse). By seeing how their impulse values actually translate while performing activities, athletes can make necessary changes in order to maximize performance by not wasting energy in the wrong directions. The impulses can be analyzed in all three dimensions, which may useful in sports in which displacements occur in more than one plane.

The body representation area 804 may include various virtual representations of a user wearing, e.g., two arm sleeves 10, two gloves 20, two leg sleeves 30, two socks 40, and chest piece 50. As explained above, one or more of the sleeves 10, gloves 20, leg sleeves 30, socks 40, and chest piece 50 may be omitted, which would be consequently reflected in the body representation area 804. The user's segments (e.g., arm, forearm) and joints may be modeled. Portions of the body may be highlighted with different colors to illustrate which part of the body is fatiguing. In one example, red may indicate a high level of fatigue, yellow may indicate a moderate level of fatigue, and green may indicate normal or not fatiguing.

In the example shown in FIG. 8C, a front view representation 810, a rear view representation 812, and a side view representation 814 may be shown in body representation area 804. The representations 810, 812, and 814 may be static or dynamic. The representations 810, 812, and 814 may be used to provide feedback to the user. For example, indicators such as different colors, highlighting, arrows, or the like may be used to highlight particular areas relating to problematic gait, body abnormalities, and/or biomechanical issues for a particular user. The representations may be able to provide animations over time of the user's movements based on the sensed movements from the sensors of kit 600. Additional visuals and detailed numbers on all the feedback may be provided in some examples. Visuals for both lay persons as well as those for experts who wish to remotely analyze specific types of activities and provide professional and medical advice to those who want such services may be displayed.

Learning Database

All of the above collected data may be securely stored in a database that can be provided to other industries that can use the information to facilitate development. This database also can be used to find biomechanical patterns within its customer demographic to facilitate research and future innovation in other associated industries. The database may include a variety of biomechanical parameters from multiple different body types. The database may include data collected from many different body types. This may be used to determine how different body types contribute to or otherwise create particular biomechanical results. This information may be used to facilitate industries like prosthetics, orthotics, and other related industries to create functional products. This can extend from joint forces and torques created by a particular human body type or activity on flat surface, inclined running, jumping, swimming, etc.

Any aspect set forth in any example may be used with any other example set forth herein. It will be apparent to those skilled in the art that various modifications and variations can be made in the disclosed systems and processes without departing from the scope of the disclosure. Other examples of the disclosure will be apparent to those skilled in the art from consideration of the specification and practice of the disclosure disclosed herein. It is intended that the specification and examples be considered as exemplary only.

We claim:

1. A system for collecting data related to user movements, comprising:

a plurality of wearable garments, wherein at least one garment comprises at least two sensors configured to collect data related to movement of a corresponding portion of the user in two or more dimensions, wherein a first sensor of the at least two sensors is configured for positioning on a first side of a joint of the user, and wherein a second sensor of the at least two sensors is configured for positioning on a second side of the joint opposite to the first side;

one or more data storage devices storing instructions for processing the data; and one or more processors configured to execute the instructions to perform a method, including:

for each sensor of the at least two sensors, receiving the data and analyzing the data to:

calculate a global orientation of the corresponding portion of the user in two or more dimensions, and converting the global orientation of the corresponding portion of the user in two or more dimensions to a local orientation of the corresponding portion of the user in two or more dimensions within a user-specific coordinate system;

calculate a horizontal impulse and a vertical impulse generated in the two or more dimensions within the user-specific coordinate system for the first and second sensors;

based on the global orientation, the local orientation, the horizontal impulse, and the vertical impulse, generating feedback associated with the movement, wherein the feedback includes a joint force and a joint torque indicative of gait, body, or biomechanical issues;

sending the feedback to a mobile device; and providing the feedback to the user via a display on the mobile device, wherein the feedback includes graphical or visual representations of received and analyzed performance and movement data for each individual sensor or a plurality of sensors such that the feedback includes representations of the user's body in two or more dimensions with indicators to highlight a particular portion of the representation of the body representing a problematic gait, one or more body abnormalities, or other biomechanical issue for that portion, and wherein the feedback further includes one or more graphs displayed for a particular joint or portion of the body, with the one or more graphs displayed next to the particular joint or portion of the body.

2. The system of claim 1, wherein the user-specific coordinate system is determined based, at least in part, on a height of the user and a waist size of the user.

3. The system of claim 1, wherein the at least one garment includes a sleeve configured to be positioned on at least one of an arm or a leg of the user.

4. The system of claim 1, wherein the at least one garment includes a sock configured to be positioned on a foot of the user, and wherein the at least two sensors configured to collect data are configured to be positioned adjacent a dorsal surface of the foot.

5. The system of claim 1, wherein the at least one garment includes a glove configured to be positioned on a hand of the user, and wherein the at least two sensors configured to collect data are configured to be positioned adjacent a dorsal surface of the hand.

6. The system of claim 1, wherein the at least one garment includes a chest piece.

7. The system of claim 1, wherein the at least one garment includes a wireless transmitter configured to transmit the data collected by the at least two sensors.

8. The system of claim 1, wherein each of the at least two sensors comprises at least one of an accelerometer, a gyroscope, and a magnetometer, and wherein the at least one garment includes an adjustable strap.

9. The system of claim 1, wherein the generated feedback further comprises information related to one or more of: ground reaction force, body portion orientation, or total body orientation.

10. The system of claim 1, wherein the plurality of wearable garments includes:
a sleeve configured to be positioned on at least one of an arm or a leg of the user, wherein the sleeve comprises a first sleeve sensor configured to collect data and configured to be positioned on a first side of a joint, and a second sleeve sensor configured to be positioned on a second side of a joint;
a sock configured to be positioned on a foot of the user, wherein the sock comprises at least one sock sensor configured to collect data and configured to be positioned adjacent a dorsal surface of the foot, and the sock further includes a plurality of pressure sensors configured to be positioned adjacent a plantar surface of the foot;
a glove configured to be positioned on a hand of the user, wherein the glove comprises at least one glove sensor configured to collect data and configured to be positioned adjacent a dorsal surface of the hand, and the glove further includes a plurality of pressure sensors configured to be positioned adjacent a palmar surface of the hand; and
a chest piece.

11. The system of claim 10, wherein the sleeve is a first sleeve configured to be positioned on a left arm of the user, and the system further includes a second sleeve configured to be positioned on a right arm of the user, a third sleeve configured to be positioned on a left leg of the user, and a fourth sleeve configured to be positioned on a right leg of the user;
the sock is a first sock and the foot is a left foot, and the system further includes a second sock configured to be positioned on a right foot of the user; and
the glove is a first glove and the hand is a left hand, and the system further includes a second glove configured to be positioned on a right hand of the user.

12. The system of claim 10, wherein a first pressure sensor of the plurality of pressure sensors of the sock is configured to be positioned adjacent a heel of the foot, and a second pressure sensor and a third pressure sensor of the plurality of pressure sensors of the sock are configured to be positioned adjacent a ball of the foot.

13. The system of claim 10, wherein the chest piece includes a hub, and the hub is configured to receive the data from the sleeve, the sock, and the glove.

14. The system of claim 10, wherein the sensors of each garment are operatively connected to: a memory, a microcontroller with a wireless communication module, and a battery.

15. A system for collecting data related to user movements, comprising:
a plurality of wearable garments, wherein at least one garment comprises at least two sensors configured to collect data related to movement of a corresponding portion of the user in two or more dimensions, wherein a first sensor of the at least two sensors is configured to be positioned on a first side of a joint, wherein a second sensor of the at least two sensors is configured to be positioned on a second side of the joint;
one or more data storage devices storing instructions for processing the data; and
one or more processors, and wherein the one or more processors are configured to execute the instructions to perform a method, including:
for each sensor of the at least two sensors, receiving the data and analyzing the data to:
determine an orientation of the corresponding portion of the user within a user-specific coordinate system, wherein the user-specific coordinate system is based on at least one sample user activity;
based on the at least one sample user activity, calculate a horizontal impulse and a vertical impulse generated in at least two dimensions within the user-specific coordinate system for each sensor of the at least two sensors;
generate feedback based on the orientation of the corresponding portion of the user, the horizontal impulse, and the vertical impulse, wherein the feedback comprises a joint force and a joint torque indicative of body movement or biomechanical issues, and wherein the generated feedback further comprises mechanical fatigue and local calorie burn for an individual muscle or individual muscle group that is less than the user's full body, wherein the mechanical fatigue is determined by detecting changes in accelerometer data, changes in orientation data, and changes in relative or absolute angles for a particular portion of the user within the user-specific coordinate system, and wherein generating the feedback further includes calculating the mechanical fatigue with respect to time by analyzing one or more specific muscular areas or muscle groups around one or more specific joints to determine if one or more muscular areas or muscle groups are speeding up or slowing down over time;
sending the feedback to a display device; and
providing the feedback to the user via the display device, and
wherein the feedback further includes graphical or visual representations of received and analyzed performance and movement data for each sensor such that the feedback includes representations of the user's body in two or more dimensions with indicators to highlight a particular portion of the representation of the body representing a problematic gait, one or more body abnormalities, or other biomechanical issue for that portion, and wherein the feedback further includes one or more graphs displayed for a particular joint or portion of the body, with the one or more graphs displayed next to the particular joint or portion of the body.

16. The system of claim 15, wherein the at least one sample user activity includes sitting or standing for a period of time.

17. The system of claim 15, wherein the at least one sample user activity comprises running, and wherein the step of generating feedback further comprises calculating a gait analysis.

18. A system for collecting data related to user movements, comprising:
a plurality of wearable garments, wherein each garment includes at least one sensor configured to collect data related to movement of a corresponding portion of the user in two or more dimensions, and the at least one sensor includes an accelerometer, a gyroscope, and a magnetometer;
one or more data storage devices storing instructions for processing the data; and
one or more processors configured to execute the instructions to perform a method, including:
for each at least one sensor, receiving the data and analyzing the data to a) determine an orientation of the corresponding portion of the user within a user-specific coordinate system, b) calculate an acceleration of each at least one sensor, c) using the acceleration data in conjunction with a length and a mass of the corresponding portion of the user, calculate forces acting on each sensor and d) calculate a horizontal impulse and a vertical impulse generated in the user-specific coordinate system for each sensor;
wherein the step of analyzing the data further comprises for each at least one sensor, based at least on the orientation of the corresponding portion of the user within the user-specific coordinate system, the acceleration data, the forces acting on each sensor, and the horizontal and vertical impulses, generating feedback on the user movements, wherein the feedback comprises mechanical fatigue and local calorie burn for an individual muscle or individual muscle group that is less than the user's full body, wherein the mechanical fatigue is determined by detecting changes in accelerometer data, changes in orientation data, and changes in relative or absolute angles for a particular portion of the user within the user-specific coordinate system, and wherein generating the feedback further includes calculating the mechanical fatigue with respect to time by analyzing one or more specific muscular areas or muscle groups around one or more specific joints to determine if one or more muscular areas or muscle groups are speeding up or slowing down over time;
sending the feedback to a mobile display device; and
providing the feedback to the user via a user interface on the mobile display device.

19. The system of claim 18, wherein analyzing the data further comprises processing the forces acting on each sensor to determine a center of mass of the user and a force acting on the center of mass of the user.

20. The system of claim 15, wherein the user-specific coordinate system is determined based, at least in part, on a height of the user and a waist size of the user;
wherein each of the at least two sensors on each garment comprises at least one of an accelerometer, a gyroscope, and a magnetometer;
wherein each of the sensors of each garment are operatively connected to: a memory, a micro-controller with a wireless communication module, and a battery;
wherein the generated feedback further comprises information related to ground reaction force, body portion orientation, and total body orientation; and
wherein the plurality of wearable garments includes:
a first sleeve configured to be positioned on a left an arm of the user, wherein the first sleeve comprises two first sleeve sensors configured to collect data and configured to be positioned on a first and a second side of a first joint;
a second sleeve configured to be positioned on a right arm of the user, wherein the second sleeve comprises two second sleeve sensors configured to collect data and configured to be positioned on a first and a second side of a second joint;
a third sleeve configured to be positioned on a left leg of the user, wherein the third sleeve comprises two third sleeve sensors configured to collect data and configured to be positioned on a first and a second side of a third joint;
a fourth sleeve configured to be positioned on a right leg of the user, wherein the fourth sleeve comprises two fourth sleeve sensors configured to collect data and configured to be positioned on a first and a second side of a fourth joint;
a first sock configured to be positioned on a first foot of the user, wherein the first sock comprises at least one sock sensor configured to collect data and configured to be positioned adjacent a dorsal surface of the first foot, wherein the first sock further includes a plurality of pressure sensors configured to be positioned adjacent a plantar surface of the first foot, and wherein the plurality of pressure sensors of the first sock include a first pressure sensor configured to be positioned adjacent a heel of the first foot, and a second pressure sensor and a third pressure sensor of the plurality of pressure sensors of the first sock are configured to be positioned adjacent a ball of the first foot;
a second sock configured to be positioned on a second foot of the user, wherein the second sock comprises at least one sock sensor configured to collect data and configured to be positioned adjacent a dorsal surface of the second foot, wherein the second sock further includes a plurality of pressure sensors configured to be positioned adjacent a plantar surface of the second foot, and wherein the plurality of pressure sensors of the second sock include a first pressure sensor configured to be positioned adjacent a heel of the second foot, and a second pressure sensor and a third pressure sensor of the plurality of pressure sensors of the second sock are configured to be positioned adjacent a ball of the second foot;
a first glove configured to be positioned on a first hand of the user, wherein the first glove comprises at least one glove sensor configured to collect data and configured to be positioned adjacent a dorsal surface of the first hand, and the first glove further includes a plurality of pressure sensors configured to be positioned adjacent a palmar surface of the first hand;
a second glove configured to be positioned on a second hand of the user, wherein the second glove comprises at least one glove sensor configured to collect data and configured to be positioned adjacent a dorsal surface of the second hand, and the second glove further includes a plurality of pressure sensors configured to be positioned adjacent a palmar surface of the second hand;
a chest piece including a hub configured to receive the data from the first sleeve, the second sleeve, the third sleeve, the fourth sleeve, the first sock, the second sock, the first glove, and the second glove; and a wireless transmitter configured to transmit the data collected by the sensors.

\* \* \* \* \*